United States Patent [19]
Zhong et al.

[11] Patent Number: 6,156,954
[45] Date of Patent: Dec. 5, 2000

[54] RECEPTOR-LIKE PROTEIN KINASE, RKN, AND METHOD OF USE FOR INCREASING GROWTH AND YIELD IN PLANTS

[75] Inventors: Jingping Zhong, La Jolla; Qun Zhu; Christopher J. Lamb, both of San Diego, all of Calif.

[73] Assignee: The Salk Institute for Biological Studies

[21] Appl. No.: 09/120,855

[22] Filed: Jul. 21, 1998

[51] Int. Cl.$^7$ ............... C12N 5/04; C12N 15/29; C12N 15/52; C12N 15/84; A01H 5/10

[52] U.S. Cl. ............. 800/290; 435/69.1; 435/320.1; 435/419; 435/469; 435/470; 435/471; 536/23.6; 800/287; 800/294; 800/298; 800/292; 800/293

[58] Field of Search ............... 435/69.1, 320.1, 435/410, 419, 468, 471, 469, 470; 536/23.6; 800/278, 287, 290, 295, 298, 320.2, 294, 292, 293

[56] References Cited

FOREIGN PATENT DOCUMENTS

WO91/15585  10/1991  WIPO ............. C12N 15/31

OTHER PUBLICATIONS

Dwyer et al., "A Superfamily of S Locus–Related Sequences in Arabidopsis: Diverse Structures and Expression Patterns," *The Plant Cell*, vol. 6, 1829–1843 (Dec. 1994).

Lease et al., "Challenges in understanding RLK function," *Cell signalling and gene regulation*, pp. 388–392.

Coello et al., "Biochemical characterization and expression of RLK4, a receptor–like kinase from *Arabidopsis thaliana*," *Plant Science* 142 (1999) pp. 83–91.

Sukhapinda et al., "Trangenic tomato (*Lycopersicon esculentum* L.) transformed with a binary vector in *Agrobacterium rhizogenes*: Non–chimeric origin of callus clone and low copy numbers of integrated vector T–DNA," *Mol Gen Genet* (1987) 206:491–497.

John C. Walker, "Receptor–like protein kinase genes of *Arabidopsis thaliana*," *The Plant Journal* (1993) 3(3), 451–456.

Hain et al., "Disease resistance results from foreign phytoalexin expression in a novel plant," *Letters to Nature*, vol. 361, pp. 153–156 (Jan. 14, 1993).

Clark et al., "The *Clavata1* Gene Encodes a Putative Receptor Kinase That Controls Shoot and Floral Meristem Size in Arabidopsis," *Cell*, 89:575–585 (1997).

Song et al., "A Receptor Kinase–Like Protein Encoded by the Rice Disease Resistance Gene, XA21," *Science*, 270:1804–1806 (1995).

Torii et al., "The Arabidopsis *ERECTA* Gene Encodes a Putative Receptor Protein Kinase with Extracellular Leucine–Rich Repeats," *The Plant Cell*, 8:735–746 (1996).

Walker, J.C., Plant Mol. Biol., vol. 26, pp. 1599–1609, 1994.

Lange et al, Plant Sci., vol. 142, pp. 133–145, 1999.

Walker, J.C., Plant J., vol. 3, pp. 451–456, 1993.

GenBank Acc. No. X89226, 1996.

*Primary Examiner*—Elizabeth F. McElwain
*Assistant Examiner*—Ashwin D. Mehta
*Attorney, Agent, or Firm*—Gray Cary Ware & Freidenrich LLP; Lisa A. Haile

[57] ABSTRACT

The present invention is based on the discovery that increased growth and yield in plants can be achieved by elevating the level of receptor-like protein kinase (RKN), a member of the receptor-like protein kinase (RLK) family. RKN polypeptide and polynucleotides encoding RKN polypeptide are provided, as are RKN expression control sequences. Also included are methods of producing a genetically modified plant characterized as having increased growth and yield as compared to a corresponding wild-type plant. A method for genetically modifying a plant cell such that a plant produced form the cell will have a modulated yield is also provided. A method of producing a genetically modified plant characterized as having increased expression of a gene product of interest in its roots as compared to the corresponding wild type plant is also provided. The invention also provides plants, plant tissue, and seeds produced by the genetically modified plants of the invention.

31 Claims, 18 Drawing Sheets

```
           10         20         30         40
   1 AAGCTTGTGT ATATGCTCGT TCCAAGCTAC ACATCATATT
  81 ACGCCATCCT TTCTTTCAGT AGAAACATGT GTAAGATCGT
 161 TTTTTTGCTT ATTCCGGAGG TTTTTTTTGA ATTTCAATGG
 241 ATGAAAATGT ATCTCATTGA ATTCATATAT TTTTAATGCC
 321 GTACTAATTA GGAGAAACTT TACCACTCTT AAAGAGATAC
 401 TTACTATACA AGATGTACTT CTAATACATA GGTCAAATTA
 481 TACTTCCCTC CATTTTATAT TATAAGTTGT TTTAACTTTT
 561 AAACATATTA GCCAAAATAT ATTTAATGTT AGATTTAAGG
 641 TTTGATAAAT CAAAACACTT ATAATATGAA ACGGAGAACC
 721 AATTCCAAGA AAACCCCTAT GAAATTCATG GGTTCCAAAA
 801 CTGTCAATTA ACAGAGTTAA TGGCATTATC AGATCACAGA
 881 ATTGATTTGA AGTAGCAAAT GCAAGGAACA AAGAGGAGAA
 961 CACCCAAAAC CATCTCTTTC CAAAGCGAAG CCGACCACCG
1041 TCTCCTCCCT TCGACTCCTC CTCCTCCCCC CTCCGACCTC
1121 CACCACCTTT CCCGCCTCCA TTTTACCACC ACCCCTCCT
1201 CCGCCGCCGC CGTCCATGTC CTGCTTTTGC TGCTGCCTCT
1281 CTCGCGCTGC TGTCGCTGAG GTCGTCGCTG GGCGACCCCG
1361 CGCGGGCGCC ACCAGGTCGC TGGCGCCGCC GTGGTGCGCG
1441 TCGGGGTCGA CCTGTCGCGG CGGAACCTGT CCGGCACCGT
1521 TCGCTGAACC TCAGCGGGAA CGGTTCGCCG GCGAGCTCCC
1601 TAGCCATAAC TTCTTCAACT CCACGTTCCC CGACGGCATC
1681 ACTGCTTCGT CGGGGAGCTC CCCCGTGGCA TCGGCGAGCT
1761 AACGGGAGCA TCCCCGGCGA GGTCGGGCAG CTGCGGCGGC
1841 GCTGCCGAGG GAGCTCGGCG AGCTCACGTC GGTCGAACAC
1921 AGTTCGGGAA GATGGCACAG CTCCGGTACC TCGATATCGC
2001 GGACTCACGC GGCTTGAATC TCTGTTCCTG TTCAAGAACA
2081 AGCGCTCCAG GTTCTCGACG TCTCGGACAA CCACCTCGCC
2161 CGCTGAATCT CATGAGCAAC TCCCTCTCCG GCACGATCCC
2241 CTATGGAACA ACTCGCTCGC CGGGAGGCTG CCGGAGTCGC
2321 GAACTCCCTC TCCGGCCCGA TTCCTCCGG TGTCTGCGCC
2401 TCGACTCCGC GATTCCGGCG AGCCTCGCCG ACTGCTCGTC
2481 GAGATTCCAG CGGGGTTCGG CGCGATACGG AATCTGACGT
2561 TCCGGCCGAC CTGGTCGCTT CTCCCAGCCT TGAGTACTTC
```

FIG. 2A

```
            50         60         70         80
     CAGATGCGGT CTGGTCGGCG AGCTCCCGGC GTTCGGCGCC
     ACGCGCTGGG CGGCGGGATC CCCGGCGACA TTGGCAGCTG
     ACCGGAGAGA TACCGGCGGC GATCGCGCTG CCGTCGATCA
     CGCCGGGGTT CACCAACTGC ACGACGTGGA GACGTTCGAC
     ACGCCGGCGA ACGCGGCAGC CCGCGCGGCA CACGGCGGCG
     GTGGTGCTCG CGGGCACCGC GCGCTGGCTG CAGTGGCGTG
     CGGCGCGCGC CACCCCGACC TCGTCGTCGG GCCGTGGCGG
     TGCCGAGGTG CGTCGAGGGG AGCGACGGCA TCGTCGGCGC
     GGCGAGGTCA TCGCCGTGAA GAAGCTGTGG CAGGCGGCGG
     GCTCCGGCAA GACAGCGACG GCGGCGGCGG CGGCAAGAGG
     GCAACATCGT CCGGCTGCTG GGGTGGTGCA CCAACGGCGA
     CTCGACGAGC TCCTCCACGC CCGCGCCAAG GCGCCGCGGG
     CGTCAGCTAC CTCCACCACG ACTGCCTCCC CGCCATCGCG
     CATGGAGGCA CGCGCTCGCC GACTTCGGCG TCGCCAAGGC
     TGCGGCTACA TTGCACCAGG TGAGCCGCAT ACACATCATC
     GTTATAAGAC TTTCTAACAT TGCCCACATA TCATATATAT
     GATTCATTAA CATATATATG AATGTGGGTA ATACTAGAAA
     TTTATTTTTG TCATTTTCTA AGAGTACACG TACACTCTAA
     ACTATTGGAG ATCCTGACGG GACGGCGGTC GGTGGAGGCG
     GGAAGGTGGC CGGAGGCGGG GTGGGCGACG TGATCGACGC
     GAGATGGCGC TGGCGTTAGG GTGGCGCTGC TGTCACCAGC
     CATGCTGCAG GAGGCCAGGC CGAAACGGAA GAACTCGGCC
     AGCAGAAAGA AGAACTAATA TATATGGTGT GCTCTTCGTG
     ACTGTCATGA ATGGGCTTGC ATATTCTTG AGCAATTTTC
     CTTGTTTTAA ACTGTGTAAT TGTATTCAGT TATGATGACC
     ATCTTGTTTA TTGATAAGTT ACTCGGATAG CAGTGAAACC
     AATGTGCTGA AAATACTAAC GGCCTCCAAC TTAATGGTAA
```

*FIG. 2B*

| | | | | | | | | | |
|---|---|---|---|---|---|---|---|---|---|
| A | MPQPQCTTTATTFPASILPPPPPPPRTTSTTSATAM | | | | | | | | 36 |
| | AAAAVHVLLLLLPLATITSASS | | | | | | | | 58 |
| B | APLPLLALLSLRSSLGDPAGALRSWTYAAAASAGAT | | | | | | | | 94 |
| | RSLAPPW | | | | | | | | 101 |
| | CAWPGVAC | | | | | | | | |
| C | DGA | TGE | VVG | VD | LSRR | NL | SG | TVS | PTA | 134 |
| | ARL | LSPT | LTS | LN | LSG | NG | SP | ASS | RR | 158 |
| | VLL | LRR | LVA | LD | VSH | NF | FN | STF | PDG | 182 |
| | IAK | LGG | FAF | LD | AFS | NC | FV | GEL | PRG | 206 |
| | IGE | LRR | LEH | LN | LGG | SF | FN | GSI | PGE | 230 |
| | VGQ | LRR | LRF | LH | LAG | NR | LS | GRL | PRE | 254 |
| | LGE | LTS | VEH | LE | IGY | NA | YD | GGI | PE | 277 |
| | FGK | MAQ | LRY | LDI | AAA | N- | VS | GPV | PPE | 301 |
| | LGG | LTR | LES | LF | LFK | NR | I- | GRRD | PPR | 325 |
| | WSR | LRA | LQV | LD | VSD | NH | LA | GAI | PA | 348 |
| | LGE | LTN | LTT | LN | LMS | NS | LS | GTI | PAA | 372 |
| | IGA | LPS | LEV | LQ | LWN | NS | LA | GRL | PES | 396 |
| | LGA | SRR | LVR | LD | VST | NS | LS | GPI | PPG | 420 |
| | VCA | GNR | LAR | LI | LFD | NR | FD | SAI | PAS | 444 |
| | LAD | CSS | LWR | VR | LEA | NR | LS | GEI | PAG | 468 |
| | FGA | IRN | LTY | MD | LSS | NS | LT | GGGI | PAD | 493 |
| | LVA | SPS | LEY | FN | VSG | N- | LV | GRPL | PDM | 517 |
| | AWR | GPK | LQV | FA | ASR | CG | LV | GEL | PAFG | 542 |
| | ATG | CAN | LYR | LE | LAG | NA | LG | GGI | PGD | 566 |
| | IGS | CKR | LVS | LR | LQH | NE | LT | GEI | PAA | 590 |
| | IAL | PSI | TEV | DL | SGT | RS | PA | PSA | G | 612 |
| | VHQ | LHD | VET | FD | VSF | NH | LA | PAE | PSS | 636 |
| | DAGERGSPRGTRRR | | | | | | | | | 650 |
| | CGCPPWRC | | | | | | | | | |
| D | AFAGMVVLAGTARWLQWRGGDDTAAADARGPGGARH | | | | | | | | | 694 |
| E | PDLVVGPWRMTAFQRLSFTADDVPRCVEGSDGIVG | | | | | | | | | 729 |
| | AGSSGTVYRAKMPNGEVIAVKKLWQAAAQKEAAAP | | | | | | | | | 764 |
| | TEQNQKLRQDSDGGGGGKRTVAEVEVLGHLRHRNI | | | | | | | | | 799 |
| | VRLLGWCTNGESTMLLYEMPNGSLDELLHARAKA | | | | | | | | | 835 |

FIG. 4-A

```
PRAGTPGTRSPSVAQGVSYLHHDCLPAIAHRDIKP         869
SNILSTTTWRHALADFGVAKALQSAAPMSVVAGSC         904
GYIAP/EYTYTLKVNEKSDVYSFGVVLLEILTGRR         938
SVEAEYGEGNNIVDWVRRKVAGGGVGDVIDAAAWA         973
DNDVGGTRDEMALALGWRCCHQPVPQERPSMREVL        1008
SMLQEARPKRKNSAKKQVKZ                       1028
```

FIG. 4-B

```
LRR No.
1                VVG VD  LSRR NL SG TVS  PTA  134
2    ARL LSPT LTS LN  LSG  NG SP ASS  RR   158
3    VLL LRR  LVA LD  VSH  NF FN STF  PDG  182
4    IAK LGG  FAF LD  AFS  NC FV GEL  PRG  206
5    IGE LRR  LEH LN  LGG  SF FN GSI  PGE  230
6    VGQ LRR  LRF LH  LAG  NR LS GRL  PRE  254
7    LGE LTS  VEH LE  IGY  NA YD GGI  PE   277
8    FGK MAQ  LRY LDI AAA  N- VS GPV  PPE  301
9    LGG LTR  LES LF  LFK  NR I- GRRD PPR  325
10   WSR LRA  LQV LD  VSD  NH LA GAI  PA   348
11   LGE LTN  LTT LN  LMS  NS LS GTI  PAA  372
12   IGA LPS  LEV LQ  LWN  NS LA GRL  PES  396
13   LGA SRR  LVR LD  VST  NS LS GPI  PPG  420
14   VCA GNR  LAR LI  LFD  NR FD SAI  PAS  444
15   LAD CSS  LWR VR  LEA  NR LS GEI  PAG  468
16   FGA IRN  LTY MD  LSS  NS LT GGGI PAD  493
17   LVA SPS  LEY FN  VSG  N- LV GRPL PDM  517
18   AWR GPK  LQV FA  ASR  CG LV GEL  PAFG 542
19   ATG CAN  LYR LE  LAG  NA LG GGI  PGD  566
20   IGS CKR  LVS LR  LQH  NE LT GEI  PAA  590
21   IAL PSI  TEV DL  SGT  RS PA PSA  G    612
22   VHQ LHD  VET FD  VSF  NH LA PAE  PSS  636

Backbone*LXX LXX LXX LX LXX NX LX GXI PXX
```

*: In the backbone of 24-amino acid leucine-rich repeat (LRR), L is often replaced by I, F, or V, and I by L, F, or V; "X" indicates any amino acid.

FIG. 5

```
  1 VVGVDLSRRNLSGTVSPTAARL-----------------------------LS----- RKN-LRR.
  1 ----------------------------------------------------------P RLK-5-LRR
  1 ---------------------------------------------------------- ERECTA-LRR
  1 VVKLLLRSSNLSGIISPSLGNLSFLRELDGDNYLSGEIP Xa-21-LRR
 25 -------PLTSLNLSGNGSPASSRRVLL--LRRIVALDVS RKN-LRR.
  2 SILCHLPSLHSISLYNNSINGSLSADDEDTCHNLISLDLS RLK-5-LRR
  1 -------------LNLSDLNLDGEISPA--IGDLKSLLSLDLR ERECTA-LRR
 41 PELSRLSRLQLELSDNSIQGSI-PAAIGACTKLTSLDLS Xa-21-LRR
 57 HNFFNSTFPDGIA-KEGGFAFLDAFSNCFVGELPRGTGEL RKN-LRR.
 42 ENLLVGSIPKSLPENLPNLKFLEISGNNLSDTIPSSFGEF RLK-5-LRR
 29 GNRLSGQIPDEIG--DCSSLQNLDLSFNELSGDIPFSISKL ERECTA-LRR
 80 HNQLRGMIPREIGASLKHLSNLYLYKNGLSGEIPSAIGNL Xa-21-LRR
 96 RRLEHLNLGGSFENGSIPGEVGQLRRIRFLHLAGNRLS-G RKN-LRR.
 82 RKLESLNLAGNFLSGTIPASLGNVTTLKELKLAYNLFSPS RLK-5-LRR
 68 KQLEQLILKNNQLIGPIPSTISQLPNLKILDLAQNKLS-G ERECTA-LRR
120 TSLQEFDLSFNRLSGAIPSSLGQISSLLTMNLGQNNLS-G Xa-21-LRR
135 RLPRELGELTSVEHLEIGYNAYDGGIPE--FGKMAQIRYL RKN-LRR.
122 QIPSQLGNLTELQVLMLAGCNLVGPIPPS-LSRLTSLVNL RLK-5-LRR
107 EIPRLIYWNEVLQYLGLRGNNLVGNISPD-LCQLTGL--- ERECTA-LRR
159 MIPNSIWNLSSLRAFSVRENKLGGMIPTNAFKTLHLLEVI Xa-21-LRR
173 DIAAANVSGPVPPELGGLTRLESLFFKNRIGRRDPPRWS RKN-LRR.
161 DLTFNQLTGSIPSWITQLKTVEQLFLFNNSFSGELPESMG RLK-5-LRR
143 ----------WYFDVR----------NNSLTGSIPETIG ERECTA-LRR
199 DMGTNRFHGKIPASVANASHLTVIQIYGNLFSGIITSGFG Xa-21-LRR
```

FIG. 6A-1

```
213 RLRALQVLDVSDNHIAGAIPA----LGELTN----LITLNL    RKN-LRR.
201 NMTTLKREDASMNKLTGKIPDNLNL-L------NLESLNL    RLK-5-LRR
162 NCIAFQVLDISYNQLTGELPFDIGFL-------QVATLSL    ERECTA-LRR
239 RLRNLTELYLWRNLFQTREQDDWGEISDLTNCSKLQTLNL    Xa-21-LRR
246 MSNSLSGTIPAAIGALP-SLEVIQLWNNSIAGRLPESLGA    RKN-LRR.
234 FENMLEGPLPESIT--RSKTLSELKLFNNRLTGVLPSQLGA   RLK-5-LRR
195 QGNQLSGKIPSVIG-LMQALAVIDLSGNLLSGSIPPILGN    ERECTA-LRR
279 GENNLGGVLPNSFSNLSTSLSFLALELNKITGSIPKDIGN    Xa-21-LRR
285 SRRLVRLD---VSTNSLSGPIPPGVCAGNRIARLIFDNR     RKN-LRR.
273 NSPLQYVDLSY--NRFSGEIPANVCGEGKIEYLILIDNS     RLK-5-LRR
234 ---LTFTEKLYLHSNKLTGSIPPEIGNMSKIHYIELNDNH    ERECTA-LRR
319 LIGLQH---LYLCNNNFRGSLPSSIGRLKNLGILLAYENN    Xa-21-LRR
322 FDSAIPASLADCSISLWRVRLEANRLSGEIPAGFGAIRNIT   RKN-LRR.
310 FSGEISNNLGRCKSITRVRLSNNKLSGQIPHGFWGLPRLS    RLK-5-LRR
271 LIGHIPPELGKITDLFDLNVANNDLEGPIPDHLSSCTNLN    ERECTA-LRR
356 LSGSIPLAIGNLIELNLILLGTNKFSGWIPYTLSNLTNLL    Xa-21-LRR
362 YMDLSNSITGGIPADIVASPSIEYF-NVSGNLVGRPLP      RKN-LRR.
350 LIELSDNSFTGS-IPKTIIGAKNLSNI-RISKNRFSGSIP    RLK-5-LRR
311 SLNVHGNKFSGT-IPRAFQKLESMTYI-NLSSNNIKGEIP    ERECTA-LRR
396 SLGLSTNNLSGP-IPSELFNIQTLSIMINVSKNNLEGSIP    Xa-21-LRR
401 DMAWRGPKLQVEAASRCGLVGELPAFGATGCANLYRIEIA    RKN-LRR.
388 NEIGSLNGIIEISGAENDFSGEIPE-STVKIKQLSRLDLS    RLK-5-LRR
349 VELSRIGNLDTLDLSNNKINGIIPS-SLGDIEHILKMNLS    ERECTA-LRR
435 QEIGHKNLVEFHAESNRLSGKIPNTLGDCQLLRYLYLQ      Xa-21-LRR
```

*FIG. 6A-2*

```
441  GNAIGGGIPGDIGSCKRIVSLRLQHNELTGEIPAAIA-LP  RKN-LRR.
427  KNQLSGEIPRELRGWKNLNELNLANNHLSGEIPKEVGILP  RLK-5-LRR
388  RNHITGVVPGDFGNLRSIMEIDLSNNDISGPIPEELNQLQ  ERECTA-LRR
474  NNLLSGSIPSALGQLKGLETLDLSSNNLSGQIPTSLADIT  Xa-21-LRR
480  SITEVDLSGTRSPAPSAGVHQLHDVETFDV-SFNHLAPAE  RKN-LRR.
467  VLNYLDLSSNQESGEIPLELQNLKLNVLNL-SYNHLSGKL  RLK-5-LRR
428  NIILRLENNLTGNVGSLANCLSLTVLNV-SHNNLVGDI   ERECTA-LRR
514  MLHSLNLSFNSEVGEVPTIGAFAAASGISIQGNAKLCGGI  Xa-21-LRR
```

FIG. 6B

```
  1  ---DGIVGAGSSGTVYRAKMPNGEVIAVKKLWQAAAQKEA   RKN-Kinase
  1  LDEKNVIGFGSSGKVYKVETRGEVVAVKKL-----NKSV    RLK-5-Kinase
  1  LSEKYIIGHGASSTVYKCVLKNCKPVATKRL-------     ERECTA-Kinase
  1  FAPTNLLGSGSFGSVYKGKINIQDHVAVKVL-------     Xa-21-Kinase
                        I 38  AAPTEQNQKIRQDSDGGGGKRTVAEVEVLGHLRHRNIVR    RKN-Kinase
 36  KGGDDEY--------------SSDSLNRDVFAAEVETLGTIRHKSIVR    RLK-5-Kinase
 32  ------Y--------------SHNPQSMKQFETELEMLSSIKHRNLVS   ERECTA-Kinase
 32  ------KL-------------ENPKALKSETAECEALRNMRHRNLVK   Xa-21-Kinase
                    II 78  ILGWCTNGES----------TMILYEYMPNGSIDELLHARAKAP-     RKN-Kinase
 70  LWCCCSSGDC----------KLLVYEYMPNGSIADVLHGDRKGG-     RLK-5-Kinase
 60  LQAYSLSHLG---E------SLIFYDYLENGSIWDLLHGPTKKK-     ERECTA-Kinase
 60  IVTICSSIDNRGNDFKAIVDFMPNGSLEDWIHPETNDQA          Xa-21-Kinase
                III                  IV 112  --RAGTPGTRSP---SVAQGVSYLHHDCLPATAHRDIKPS          RKN-Kinase
104  --VVLGWPERLRIALDAAEGLSYLHHDCVPPIVHRDVKSS          RLK-5-Kinase
 94  ---T-LDWDIRLKIAYGAAQGLAYLHHDCSPRIIHRDVKSS         ERECTA-Kinase
100  DQRHLNLHRRVTILDVACALDYLHRHGPEPVVHCDIKSS           Xa-21-Kinase
              V                    VIa           VIb
```

FIG. 7-A

```
147 NILSTTWRHALADFGVAK---------ALQSAAPMSVVAG  RKN-Kinase
142 NILLDSDYGAKVADFGIAKV-------GQMSGKTPEAMSGIAG  RLK-5-Kinase
131 NILLDKDLEARLTDFGIAK--------SLCVSKSHTS-TYVMG  ERECTA-Kinase
140 NVLLDSDMVAHVGDFGLARILVDGTSLIQQSTSSMGFI-G  Xa-21-Kinase
                          VII 179 SCGYIAPEYTYTLKVNEKSDVYSFGVVLLELLTGRRSVEA  RKN-Kinase
179 SCGYIAPEYVYTLRVNEKSDIYSFGVVLLELVTGKQPTDS  RLK-5-Kinase
165 TIGYIDPEYARTSRLTEKSDVYSYGIVLLELLTRRKAVDD  ERECTA-Kinase
179 TIGYAAPEYGVGLFASTHGDIYSYGILVLETVTGKRPTDS  Xa-21-Kinase
                          VIII                    IX 219 EYGEGNNIVDWVRRKVAGGVGDVIDAA-AWADND-VGGT  RKN-Kinase
219 ELGD-KDMAKWVCTAIDKCGLEPVIDPKLDLKFKE----EI  RLK-5-Kinase
205 E-------SNIHHLIMSKTGNNEVMEMADPDITSTCKD-LGVV  ERECTA-Kinase
219 TFRPDLGIRQYVELGIHGR-VTDVVDTKLILDSENWLNST  Xa-21-Kinase
                          X 257 RDE-----MALALGWR-------CCHQPVPQERPSMREVLSML  RKN-Kinase
255 SKV-----IHIGLI---------CTSPLNRPSMRKVVIML  RLK-5-Kinase
240 KKV-----FQLALL---------CTKRQPNDRPTMHQVTRVL  ERECTA-Kinase
258 NNSPCRRITECIVWLLRLGLSCSQFLPSSRTPTGDIIDEL  Xa-21-Kinase
                          XI
```

*FIG. 7-B*

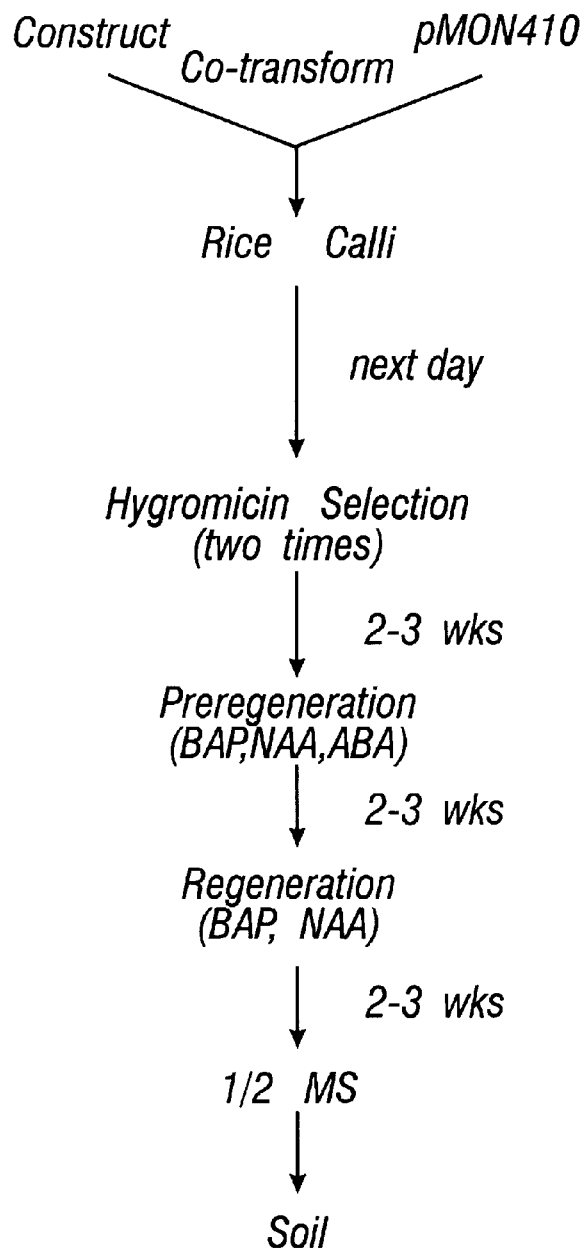
FIG. 9
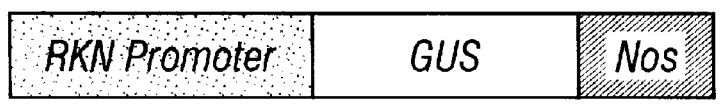
FIG. 10

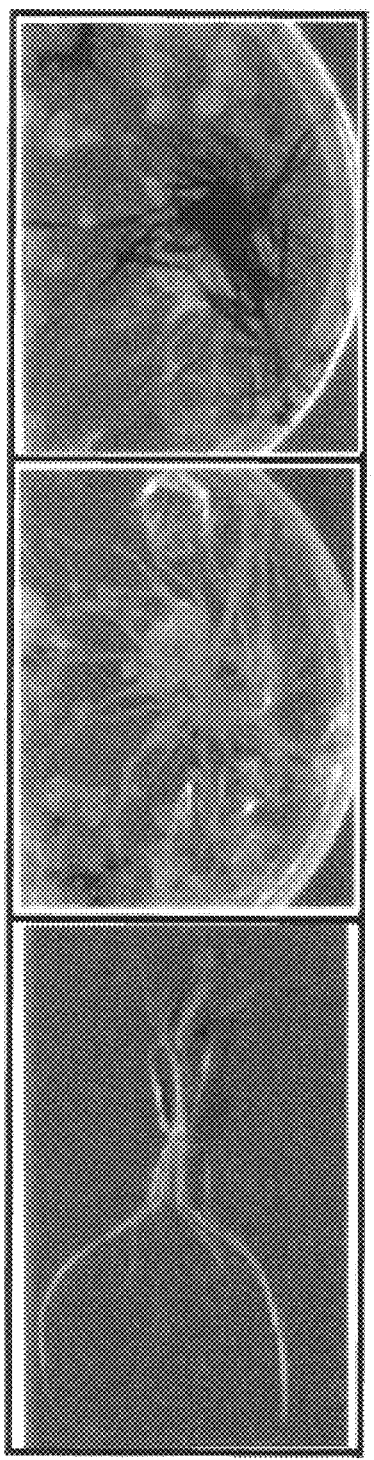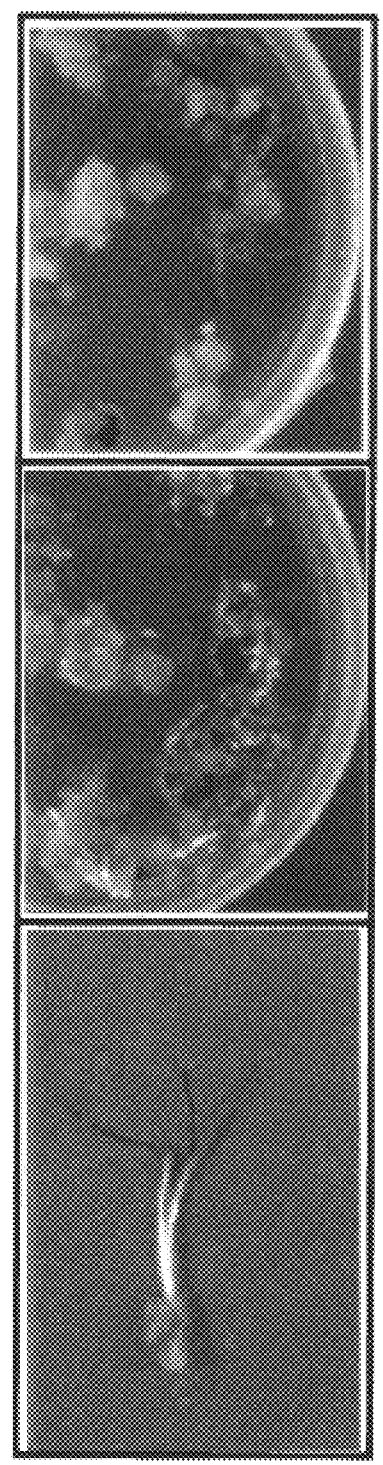
35S::RKN  WT
FIG. 12

Rice homolog of clavata 1 (Zhong, Zhu and Lamb, unpublished)
Rice Xo resistance gene (Song et al., Science 270: 1804-1806, 1995)
Steroid signal transduction/putative receptor (Li and Chory, Cell, 90, 1997)
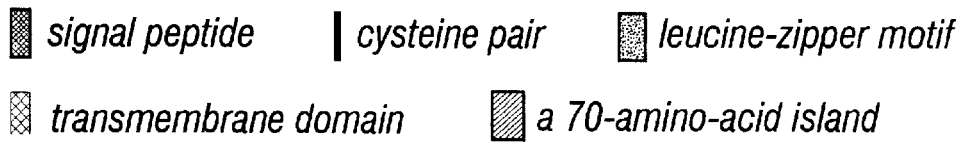
FIG. 15

RECEPTOR-LIKE PROTEIN KINASE, RKN, AND METHOD OF USE FOR INCREASING GROWTH AND YIELD IN PLANTS

FIELD OF THE INVENTION

The present invention relates generally to plant genetic engineering, and more specifically to a receptor-like protein kinase and to methods for producing genetically engineered plants characterized as having increased growth and yield utilizing the receptor-like protein kinase of the invention.

BACKGROUND OF THE INVENTION

For each plant species, there exists a wide discrepancy in plant growth due to environmental conditions. Under most conditions, the maximum growth potential of a plant is not realized. Plant breeding has demonstrated that a plant's resources can be redirected to individual organs to enhance growth.

Genetic engineering of plants, which entails the isolation and manipulation of genetic material, e.g., DNA or RNA, and the subsequent introduction of that material into a plant or plant cells, has changed plant breeding and agriculture considerably over recent years. Increased crop food values, higher yields, feed value, reduced production costs, pest resistance, stress tolerance, drought resistance, the production of pharmaceuticals, chemicals and biological molecules as well as other beneficial traits are all potentially achievable through genetic engineering techniques.

The ability to manipulate gene expression provides a means of producing new characteristics in transformed plants. For example, the ability to increase the size of a plants root system would permit increased nutrient assimilation from the soil. Moreover, the ability to increase leaf growth would increase the capacity of a plant to assimilate solar energy. Obviously, the ability to control the growth of an entire plant, or specific target organs thereof would be very desirable.

Receptors located in the plasma membrane play a prominent role in cell signaling. Recently, evidence has suggested that plant cells also carry cell surface receptors that also have protein kinase activity. The plant receptor like protein kinases (RLKs) are structurally related to the polypeptide growth factor receptors of mammals. These proteins have a large extra cytoplasmic domain, a membrane spanning segment and a cytoplasmic domain which has protein kinase activity. Most mammalian growth factor receptor protein kinases are tyrosine kinases, but many plant RLKs are serine/threonine protein kinases. The RLKs have been placed into three categories based on structural similarities: (1) S-domain proteins are related to the self-incompatibility locus glycoproteins of Brassica, (2) leucine-rich repeat proteins contain a tandemly repeated motif that has been found in numerous eukaryotic proteins, and (3) proteins which contain epidermal growth factor-like repeats. The RLKs have been found in monocotyledonous plants such as maize and in dicotyledonous plants such as Brassicaceae (for review see: Walker, J. C., 1994, "Structure and function of the receptor-like protein kinases of higher plants," Plant Mol. Biol. 26:1599–1609). The present invention provides a novel RLK, termed receptor-like protein kinase (RKN).

SUMMARY OF THE INVENTION

The present invention is based on the discovery that increased growth and yield in plants can be achieved by elevating the level of receptor-like protein kinase (RKN), a member of the RLK family.

In one embodiment, substantially purified RKN polypeptide is provided. Isolated polynucleotides encoding RKN polypeptide are also provided, as are RKN expression control sequences.

In another embodiment, the invention provides a method of producing a genetically modified plant characterized as having increased growth and yield as compared to a corresponding wild-type plant by (1) contacting plant cells with nucleic acid encoding an RKN polypeptide, operatively associated with an expression control sequence, to obtain transformed plant cells; (2) producing plants from the transformed plant cells which allow expression of RKN; and (3) selecting a plant exhibiting increased yield.

A method for genetically modifying a plant cell such that a plant produced form the cell will have a modulated yield is also provided. The method includes introducing an isolated polynucleotide encoding an RKN polypeptide and growing the transformed plant cell under conditions which permit modulation of RKN polypeptide.

In a further embodiment, a method is provided for producing a genetically modified plant characterized as having increased expression of a gene product of interest in its roots as compared to the corresponding wild type plant by (1) contacting plant cells with polynucleotide including the expression control sequence of RKN operatively linked to a region encoding the gene product of interest to obtain transformed plant cells; (2) producing plants form the transformed plant cells; and (3) selecting a plant exhibiting increased expression of the gene product of interest in its roots.

A method is also provided of producing genetically transformed, disease resistant plants by introducing into the genome of a plant cell, to obtain a transformed plant cell, a nucleic acid sequence including an expression control sequence of RKN operably linked to a polynucleotide encoding a polypeptide conferring resistance to a pathogen.

The invention also provides plants, plant tissue, and seeds produced by the genetically modified plants of the invention.

BRIEF DESCRIPTION OF THE DRAWINGS

FIG. 2 is the polynucleotide sequence of the RKN gene (SEQ ID NO:1).

FIG. 4 is the amino acid sequence of RKN polypeptide (SEQ ID NO:2).

FIG. 5 shows the alignment of the LRR repeats in the RKN protein.

FIGS. 6a and 6b show the sequence alignments of the LRR region between RKN and proteins homologous to RKN.

FIG. 7 shows a homology alignment of the cytoplasmic kinase domain of RKN with other receptor-like protein kinase domains in plants.

FIG. 9 shows a strategy for producing transgenic plants carrying the RKN gene.

FIG. 10 shows constructs used in generating transgenic plants.

FIG. 12 shows photographs of enhanced root production in 35S::RKN transformants. Root production in wild-type plants are shown for comparison.

FIG. 15 shows a comparison of three receptor-like protein kinases, RKN, Xa21, and BRI1. The locations of the signal peptide, cysteine pair, leucine-zipper motifs, transmembrane domains, kinase domains, and a 70 amino-acid island, are indicated.

DESCRIPTION OF THE PREFERRED EMBODIMENTS

Figure 1:
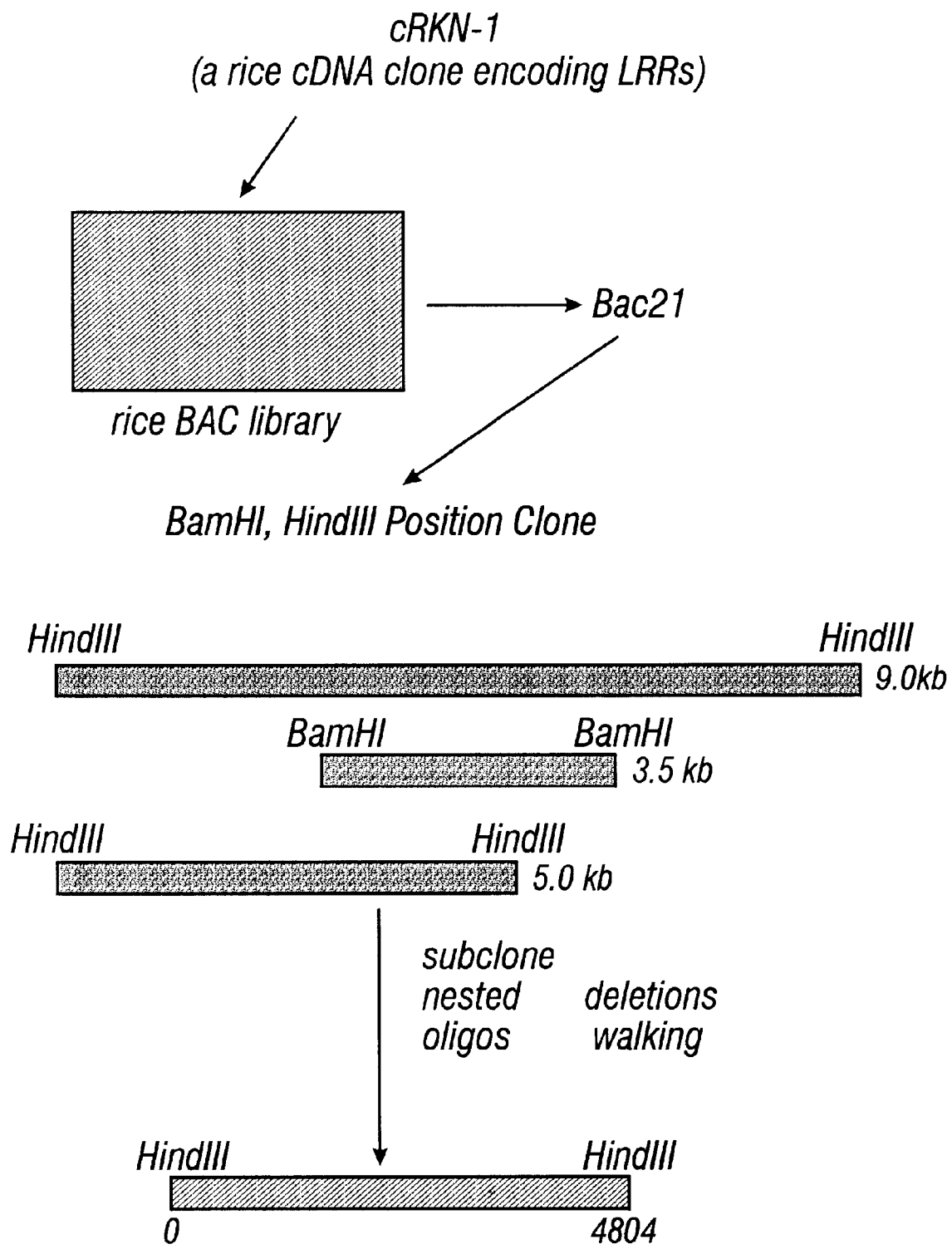
FIG. 1 illustrates the cloning strategy used for isolation of receptor-like protein kinase (RKN).

This invention provides a novel RLK, termed RKN, which is a member of the class of RLKs that contain leucine-rich repeats.

Polynucleotides, Polypeptides, Vectors, and Host Cells

The invention provides substantially purified RKN polypeptide. Preferably, RKN has an amino acid sequence set forth in SEQ ID NO:2. The term "substantially purified" as used herein refers to a polypeptide which is substantially free of other proteins, lipids, carbohydrates or other materials with which it is naturally associated. One skilled in the art can purify RKN using standard techniques for protein purification. The substantially pure polypeptide will yield a single major band on a non-reducing polyacrylamide gel. The purity of the RKN polypeptide can also be determined by amino-terminal amino acid sequence analysis.

By a "substantially pure polypeptide" is meant an RKN polypeptide which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, RKN polypeptide. A substantially pure RKN polypeptide may be obtained, for example, by extraction from a natural source (e.g., a plant cell); by expression of a recombinant nucleic acid encoding an RKN polypeptide; or by chemically synthesizing the protein. Purity can be measured by any appropriate method, e.g., those described in column chromatography, polyacrylamide gel electrophoresis, or by HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms but synthesized in *E. Coli* or other prokaryotes.

The invention includes functional RKN polypeptide as well as functional fragments thereof. As used herein, the term "functional polypeptide" refers to a polypeptide which possesses biological function or activity which is identified through a defined functional assay and which is associated with a particular biologic, morphologic, or phenotypic alteration in the cell. The term "functional fragments of RKN polypeptide," refers to all fragments of RKN that retain an RKN activity, e.g., receptor protein kinase activity. Biologically functional fragments, for example, can vary in size from a polypeptide fragment as small as an epitope capable of binding an antibody molecule to a large polypeptide capable of participating in the characteristic induction or programming of phenotypic changes within a cell. An example of a functional fragment of RKN is a polypeptide including the kinase domain of RKN (see FIG. 3 and FIG. 7). Another functional fragment of RKN is a polypeptide including the additional cytoplasmic ligand-binding domain of RKN (see FIG. 3).

Minor modifications of the RKN primary amino acid sequences may result in proteins which have substantially equivalent activity as compared to the unmodified counterpart polypeptide described herein. Such modifications may be deliberate, as by site-directed mutagenesis, or may be spontaneous. All of the polypeptides produced by these modifications are included herein as long as the biological activity of RKN still exists. Further, deletion of one or more amino acids can also result in a modification of the structure of the resultant molecule without significantly altering its activity. Deletion can lead to the development of a smaller active molecule which could have broader utility. For example, it may be possible to remove amino or carboxy terminal amino acids required for RKN activity. RKN polypeptide includes amino acid sequences substantially the same as the sequence set forth in SEQ ID NO:2. The term "substantially the same" refers to amino acid sequences that retain the activity of RKN as described herein, e.g., receptor protein kinase activity.

The invention includes polypeptides having substantially the same as the amino acid sequence set forth in SEQ ID NO:2 or functional fragments thereof, or amino acid sequences that are substantially identical to SEQ ID NO:2. By "substantially the same" or "substantially identical" is meant a polypeptide or nucleic acid exhibiting at least 60–80%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

By "substantially identical" is also meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein assayed, (e.g., as described herein). Preferably, such a sequence is at least 85%, more preferably identical at the amino acid level to SEQ ID NO:2.

Homology is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications.

The RKN polypeptides of the invention include conservative variations of the polypeptide sequence. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The invention provides polynucleotides encoding the RKN protein. These polynucleotides include DNA, cDNA and RNA sequences which encode RKN. It is understood that all polynucleotides encoding RKN are also included herein, as long as they encode a polypeptide with RKN activity. Such polynucleotides include naturally occurring, synthetic, and intentionally manipulated polynucleotides. For example, RKN polynucleotide may be subjected to site-directed mutagenesis. The polynucleotide sequence for RKN also includes antisense sequences and sequences encoding dominant negative forms of RKN. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of RKN polypeptide encoded by the nucleotide sequence is functionally unchanged.

Specifically disclosed herein is a polynucleotide sequence containing the RKN gene.

Preferably, the RKN nucleotide sequence is SEQ ID NO: 1. The term "polynucleotide" or "nucleic acid sequence" refers to a polymeric form of nucleotides at least 10 bases in length. By "isolated polynucleotide" is meant a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g. a cDNA) independent of other sequences. The nucleotides of the invention can be ribonucleotides, deoxyribonucleotides, or modified forms of either nucleotide. The term includes single and double forms of DNA.

The polynucleotide encoding RKN includes SEQ ID NO: 1, dominant negative forms of RKN, and nucleic acid sequences complementary to SEQ ID NO: 1. A complementary sequence may include an antisense nucleotide. When the sequence is RNA, the deoxynucleotides A, G, C, and T of SEQ ID NO: 1 are replaced by ribonucleotides A, G, C, and U, respectively. Also included in the invention are fragments of the above-described nucleic acid sequences and are at least 15 bases in length, which is sufficient to permit the fragment to selectively hybridize to DNA that encodes the protein of SEQ ID NO:2 under physiological conditions or a close family member of RKN. The term "selectively hybridize" refers to hybridization under moderately or highly stringent conditions which excludes non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

DNA sequences encoding RKN can be expressed in vitro by DNA transfer into a suitable host cell. "Host cells" are cells in which a vector can be propagated and its DNA expressed. The cell may be plant cells, or prokaryotic or eukaryotic cells. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the RKN polynucleotide sequences may be inserted into an expression vector. The term "expression vector" refers to a plasmid, virus or other vehicle known in the art that has been manipulated by insertion or incorporation of the RKN genetic sequences. Polynucleotide sequence which encode RKN can be operatively linked to expression control sequences. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, as start codon (i.e., ATG) in front of a protein-encoding gene, splicing signal for introns, maintenance of the correct reading frame of that gene to permit proper translation of mRNA, and stop codons. The term "control sequences" is intended to included, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the gene.

Optionally, a selectable marker may be associated with the RKN polynucleotide. As used herein, the term "marker" refers to a gene encoding a trait or a phenotype which permits the selection of, or screening for, a cell containing the marker. Preferably, the marker gene is an antibiotic resistance gene whereby the appropriate antibiotic can be used to select for transformed cells from among cells that are not transformed. Examples of suitable selectable markers for use in plants include adenosine deaminase, dihydrofolate reductase, hygromycin-B-phosphotransferase, thymidine kinase, xanthine-guanine phospho-ribosyltransferase and amino-glycoside 3'-O-phosphotransferase II (kanamycin, neomycin and G418 resistance). Other suitable markers will be known to those of skill in the art.

A variety of host-expression vector systems may be utilized to express the RKN coding sequence. These include but are not limited to microorganisms such as bacteria transformed with recombinant bacteriophage nucleic acid, plasmid nucleic acid or cosmid nucleic acid expression vectors containing the RKN coding sequence; yeast transformed with recombinant yeast expression vectors containing the RKN coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the RKN coding sequence; insect cell systems infected with recombinant virus expression vectors (e.g., baculovirus) containing the RKN coding sequence; or animal cell systems infected with recombinant virus expression vectors (e.g., retroviruses, adenovirus, vaccinia virus) containing the RKN coding sequence, or transformed animal cell systems engineered for stable expression.

RKN Regulatory Sequences

The term "RKN expression control sequence" or "RKN regulatory region" as used herein refers to the nucleotide sequence of SEQ ID NO:3, as well as complementary sequences and sequences which exhibit at least about 75% sequence identity, preferably at least about 85% sequence identity, more preferably at least about 90% sequence identity with the sequence of SEQ ID NO:3. A functional RKN expression control sequence is capable of promoting the expression of a gene operably attached thereto in an appropriate cell, such as a cells in the root of a plant. A functional RKN expression control sequence includes an RKN promoter.

RKN expression control sequences also include such elements as transcriptional start points (tsp), which can be identified by primer extension analysis. Elements well known in the art, such as a TATA box, supressors or silencers, and enhancers, and consensus sequences for elements that bind the transcription factors CTF/NF-1, AP-1, NF-κB and NF-ATp are included in the RKN expression control sequence.

Polynucleotide sequences of the invention include DNA, CDNA and RNA sequences which encode the RKN expression control sequence. It is understood that all polynucleotides encoding all or a functional portion of the RKN regulatory region are also included herein. Such polynucleotides include naturally occurring, synthetic, and intentionally manipulated polynucleotides. As an example, the RKN promoter polynucleotide may be subjected to site-directed mutagenesis. The polynucleotide sequence for the RKN regulatory region also includes antisense sequences.

Figure 3:
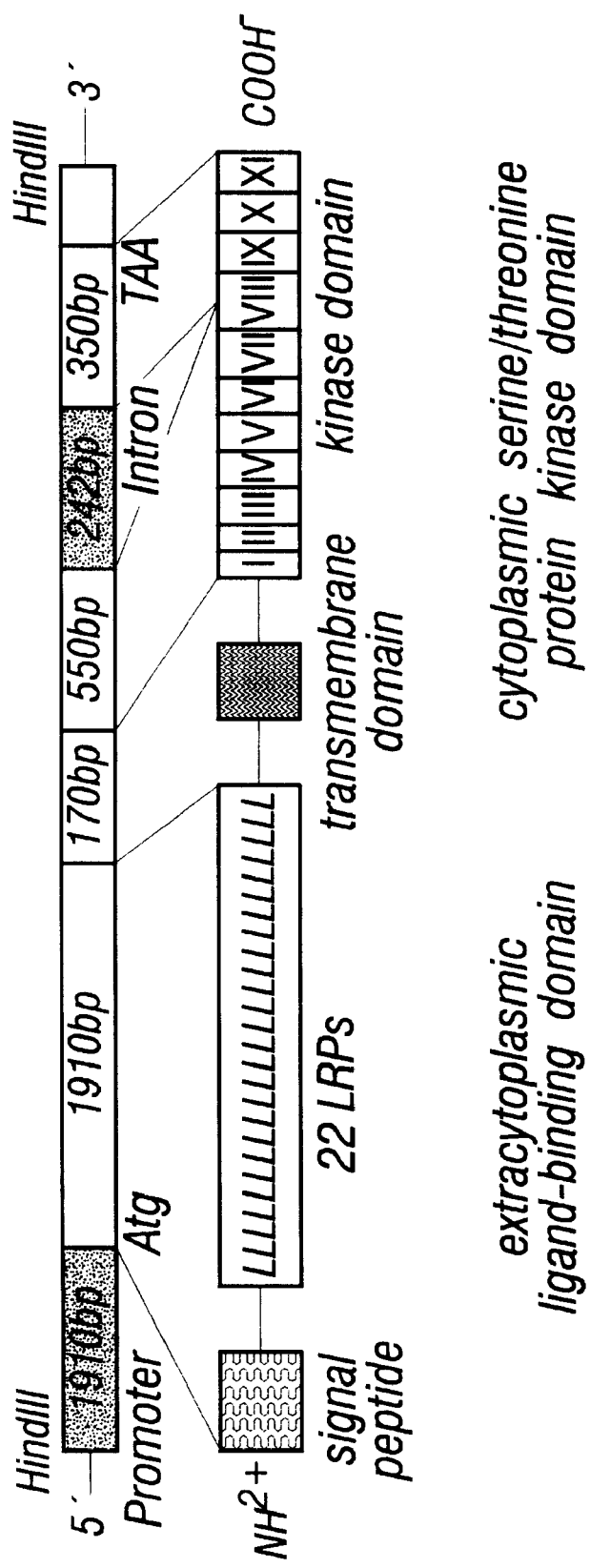
FIG. 3 shows the structure of the RKN gene and the domains of the predicted protein.
Figure 8:
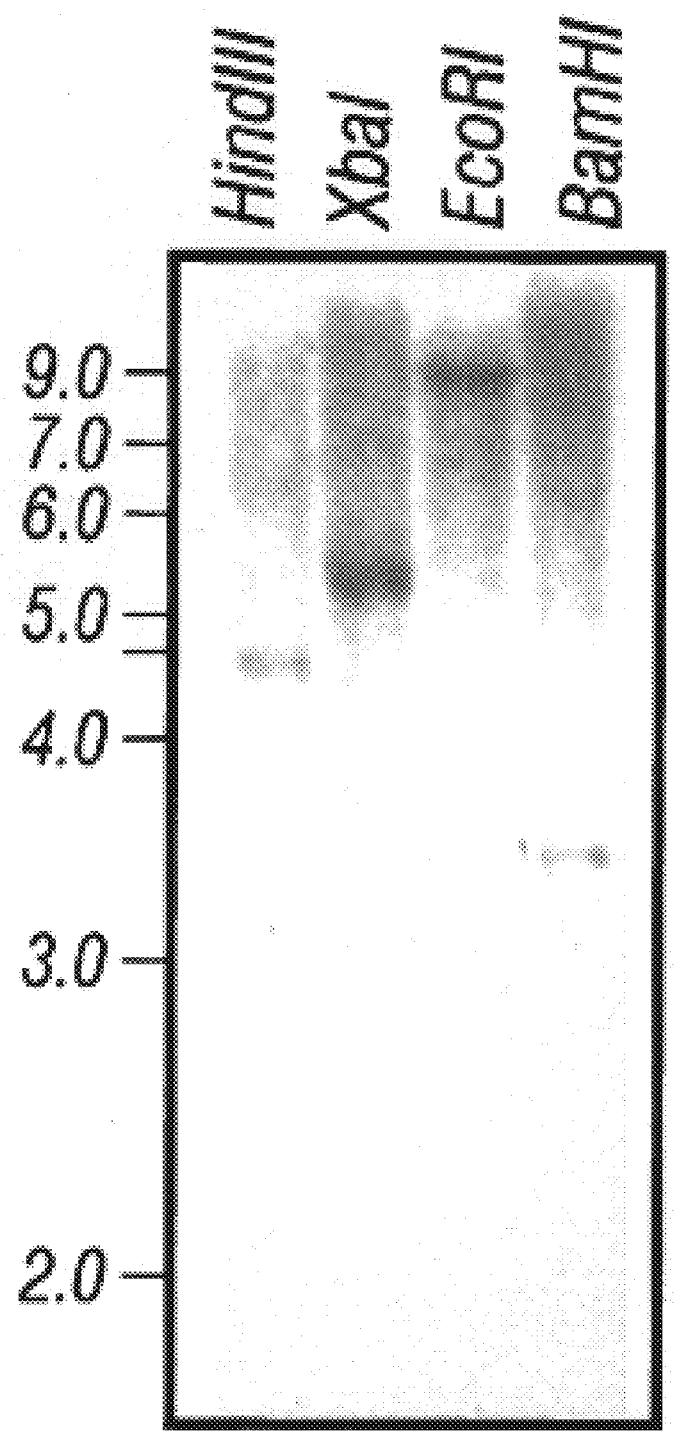
FIG. 8 shows a Southern blot of HindIII, XbaI, EcoRI and BamHI digests of genomic DNA from rice.

It should be noted that SEQ ID NO:3 includes multiple active domains, for example the promoter domain as shown in FIG. 3.

The RKN regulatory region can be operably linked to any "nucleotide sequence of interest." By "nucleotide sequence of interest" or "DNA of interest" is meant any nucleotide sequence (e.g., RNA or DNA sequence) or DNA sequence that encodes a protein or other molecule that is desirable for expression in a target cell (e.g., for production of the protein or other biological molecule, such as a therapeutic cellular product, in the target cell). The nucleotide sequence of interest includes functional RKN polypeptide and fragments thereof. The nucleotide sequence of interest can be a dominant neoative form of RKN. The nucleotide sequence of interest can be an antisense molecule or a triplex forming agent. The use of the term "DNA of interest" throughout the specification is not meant to limit the invention to deoxyribonucleic acid.

The RKN regulatory region can be operably linked to a "heterologous nucleic acid sequence." The term "heterologous nucleic acid sequence" as used herein refers to a nucleic acid foreign to the recipient plant host or, native to the host if the native nucleic acid is substantially modified from its original form.

By "gene product of interest" is meant a polypeptide, RNA molecule, or other gene product that is desired for expression in the subject. "Gene products of interest" can include, for example, polypeptides that serve as marker proteins to assess cell transformation and expression, fusion proteins, polypeptides having a desired biological activity, gene products that can complement a genetic defect, RNA molecules, transcription factors, and other gene products that are of interest in regulation and/or expression. "Gene products of interest" include RKN polypeptides, antisense nucleic acids, triplex forming agents, and ribozymes. "Gene products of interest" also include nucleotide sequences that provide a desired effect or regulatory function, but do not necessarily encode an RNA molecule or polypeptide per se (e.g., transposons, introns, promoters, enhancers, splice signals, etc.).

Antisense nucleic acids are DNA or RNA molecules that are complementary to at least a portion of a specific mRNA molecule (Weintraub, 1990, Scientific American, 262:40). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target FT-producing cell. The use of antisense methods to inhibit the in vitro translation of genes is well known in the art (Marcus-Sakura, 1988, Anal. Biochem., 172:289).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., 1991, Antisense Res. and Dev., 1(3):227; Helene, C., 1991, Anticancer Drug Design, 6(6):569).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, 1988, J. Amer. Med. Assn., 260:3030). A major advantage of this approach is that, because they are sequence-specific, only mRNAs with particular sequences are inactivated.

There are two basic types of ribozymes namely, tetrahymena-type (Hasselhoff, 1988, Nature, 334:585) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences. "Operably linked" is defined above. By "operatively inserted" is meant that the DNA of interest is positioned adjacent a DNA sequence that directs transcription and translation of the introduced DNA (i.e., facilitates the production of, e.g., a polypeptide encoded by a DNA of interest).

RKN Antibodies

The RKN polypeptides of the invention can be used to produce antibodies which are immunoreactive or bind to epitopes of the RKN polypeptides. Antibodies directed against peptides derived from the extracellular domain of RKN are preferred (e.g., peptides contained in the domain shown in FIG. 3). Antibodies which consist essentially of pooled monoclonal antibodies with different epitopic specificities, as well as distinct monoclonal antibody preparations are provided.

The preparation of polyclonal antibodies is well-known to those skilled in the art. See, for example, Green et al., 1992, "Production of Polyclonal Antisera," in: *Immunochemical Protocols (Manson, ed.), pages 1–5* (Humana Press); Coligan et al., 1992, "Production of Polyclonal Antisera in Rabbits, Rats, Mice and Hamsters," in: *Current Protocols in Immunology*, section 2.4.1, which are hereby incorporated by reference.

The preparation of monoclonal antibodies likewise is conventional. See, for example, Kohler and Milstein, 1975, Nature 256:495; Coligan et al., sections 2.5.1–2.6.7; and Harlow et al., 1988, in: *Antibodies: a Laboratory Manual*, page 726 (Cold Spring Harbor Pub.), which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3; Barnes et al., 1992, "Purification of Immunoglobulin G (IgG)," in: *Methods in Molecular Biology*, Vol. 10, pages 79–104 (Humana Press).

Methods of in vitro and in vivo multiplication of monoclonal antibodies are well known to those skilled in the art. Multiplication in vitro may be carried out in suitable culture media such as Dulbecco's Modified Eagle Medium or RPMI 1640 medium, optionally supplemented by a mammalian serum such as fetal calf serum or trace elements and growth-sustaining supplements such as normal mouse peritoneal exudate cells, spleen cells, thymocytes or bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

The term "antibody" as used in this invention includes intact molecules as well as fragments thereof, such as Fab, $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, 1988, *Antibodies: A Laboratory Manual*, Cold Spring Harbor Laboratory, New York, incorporated herein by reference). As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. No. 4,036,945 and No. 4,331,647, and references contained therein. These patents are hereby incorporated in their entireties by reference. See also Nisonhoff et al., 1960, Arch. Biochem. Biophys.89:230, Porter, 1959, Biochem. J. 73:119; Edelman et al., 1967, *Methods in Enzymology*, Vol. 1, page 422 (Academic Press); and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar et al., 1972, Proc. Nat'l Acad. Sci. USA 69:2659. Alternatively, the variable chains can be linked by an intermolecular disulfide bond or cross-linked by chemicals such as glutaraldehyde. See, e.g., Sandhu, supra. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. Coli* The recombinant host cells synthesize a single polypeptide chain with a linker peptide bridging the two V domains. Methods for producing sFvs are described, for example, by Whitlow et al., 1991, *Methods: a Companion to Methods in Enzymology*, Vol. 2, page 97; Bird et at., 1988, Science 242:423–426; Ladner et al., U.S. Pat. No. 4,946,778; Pack et al., 1993), Bio/Technology 11:1271–77; and Sandhu, supra.

Another form of an antibody fragment is a peptide coding for a single complement-arity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., 1991, *Methods: a Companion to Methods in Enzymology*, Vol. 2, page 106.

Antibodies which bind to the RKN polypeptide of the invention can be prepared using an intact polypeptide or fragments containing small peptides of interest as the immunizing antigyen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g,., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., 1991, Unit 9, Current Protocols in Immunology, Wiley Interscience, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

Genetically Modified Plants and Methods of Making

In another embodiment, the invention provides a method for producing a genetically modified plant characterized as having increased yield as compared to a plant which has not been genetically modified (e.g., a wild-type plant). The term "yield" or "plant yield" refers to increased crop growth, and/or increased biomass. In a preferred embodiment, increased yield results from increased growth rate and increased root size. In another embodiment, increased yield is derived from shoot growth. The invention method comprises the steps of introducing at least one nucleic acid sequence encoding RKN into a plant cell to obtain a transformed plant cell wherein the nucleic acid sequence is operably associated with a promoter, producing a plant from the transformed plant cell under conditions which allow expression of RKN polypeptide; and thereafter selecting a plant exhibiting increased yield. The plant may be either a monocot or a dicot. Examples of monocotyledonous plants include, but are not limited to, asparagus, field and sweet corn, barley, wheat, rice (e.g., Japonica or Indica), sorghum, onion, pearl millet, rye and oats. Examples of dicotyledonous plants include, but are not limited to tomato, tobacco, cotton, rapeseed, field beans, soybeans, potatoes, grapes, strawberries, peppers, lettuce, peas, alfalfa, clover, cole crops or Brassica oleracea (e.g., cabbage, broccoli, cauliflower, brussel sprouts), radish, carrot, beets, eggplant, spinach, cucumber, squash, melons, cantaloupe, sunflowers and various ornamentals. Woody species include poplar, pine, sequoia, cedar, oak, etc.

The term "genetic modification" as used herein refers to the introduction of one or more heterologous nucleic acid sequences into one or more plant cells, to provide sexually competent, viable plants. The term "genetically modified" as used herein refers to a plant which has been generated through the aforementioned process. Genetically modified plants of the invention are capable of self-pollinating or cross-pollinating with other plants of the same species so that the foreign gene, carried in the germ line, can be inserted into or bred into agriculturally useful plant varieties. The term "plant cell" as used herein refers to protoplasts, gamete producing cells, and cells which regenerate into whole plants. Accordingly, a seed comprising multiple plant cells capable of regenerating into a whole plant, is included in the definition of "plant cell".

As used herein, the term "plant" refers to either a whole plant, a plant part, a plant cell, or a group of plant cells, such as plant tissue, for example. Plantlets are also included within the meaning of "plant". Plants included in the invention are any plants amenable to transformation techniques, including angiosperms, gymnosperms, monocotyledons and dicotyledons.

The term "heterologous nucleic acid sequence" has been defined above. Any nucleic acid sequence of interest may be used with the subject invention. For example, the term includes a nucleic acid originating in the host species, where such sequence is operably linked to a promoter that differs from the natural or wild-type promoter. In the broad method of the invention, at least one nucleic acid sequence encoding RKN polypeptide is associated to a suitable promoter. It may be desirable to introduce more than one copy of RKN polynucleotide into a plant for enhanced RKN expression. For example, multiple copies of the gene would have the effect of increasing production of RKN polypeptide in the plant allowing for greater root growth.

Genetically modified plants of the present invention are produced by introducing into a plant cell, a vector including at least one nucleic acid sequence encoding RKN. To be effective once introduced into plant cells, the RKN nucleic acid sequence must be operably associated with a promoter which is effective in the plant cells to cause transcription of RKN. Additionally, a polyadenylation sequence or transcription control sequence, also recognized in plant cells may also be employed. It is preferred that the vector harboring the nucleic acid sequence to be inserted also contain one or more selectable marker genes so that the transformed cells can be selected from nontransformed cells in culture, as described herein.

The expression of RKN polynucleotides in the present invention may be driven by a number of promoters. The endogenous, or native promoter of an RKN may be utilized for transcriptional regulation of the gene, or a heterologous promoter that is a foreign regulatory sequence may be utilized. For plant expression vectors, suitable viral promoters include the 35S RNA and 19S RNA promoters of CaMV (Brisson, et al., 1984, Nature, 310:51 1; Odell, et al., 1985, Nature, 313:810); the full-length transcript promoter from Figwort Mosaic Virus (FMV) (Gowda, et al., 1989, J. Cell Biochem., 1 3D:30 1,) and the coat protein promoter to TMV (Takamatsu, et al., 1987, EMBO J. 6:307). Alternatively, plant promoters such as the light-inducible promoter from the small subunit of ribulose bis-phosphate carboxylase (ssRUBISCO) (Coruzzi, et al., 1984, EMBO J., 3:1671; Broglie, et al., 1984, Science, 224:838); mannopine synthase promoter (Velten, et al., 1984, EMBO J., 3:2723) nopaline synthase (NOS) and octopine synthase (OCS) promoters (carried on tumor-inducing plasmids of Agrobacterium tumefaciens) or heat shock promoters, e.g., soybean hsp17.5-E or hsp17.3-B (Gurley, et al., 1986, Mol. Cell. Biol., 6:559; Severin, et al., 1990, Plant Mol. Biol., 15:827) may be used.

Promoters useful in the invention include both natural constitutive and inducible promoters as well as engineered promoters. The CaMV promoters are examples of constitutive promoters. To be most useful, an inducible promoter should 1) provide low expression in the absence of the inducer; 2) provide high expression in the presence of the inducer; 3) use an induction scheme that does not interfere with the normal physiology of the plant; and 4) have no effect on the expression of other genes. Examples of inducible promoters useful in plants include those induced by chemical means, such as the yeast metallothionein promoter which is activated by copper ions (Mett, et al., 1993, Proc. Natl. Acad. Sci., U.S.A., 90:4567); In2-1 and In2-2 regulator sequences which are activated by substituted benzeneslulfonamides, e.g., herbicide safeners (Hershey, et al., 1991, Plant Mol. Biol., 17:679); and the GRE regulatory sequences which are induced by glucocorticoids (Schena, et al., 1991, Proc. Natl. Acad. Sci., U.S.A., 88:10421). Other promoters, both constitutive and inducible will be known to those of skill in the art.

The particular promoter selected should be capable of causing sufficient expression to result in the production of an effective amount of structural gene product, e.g., RKN polypeptide, to cause increased plant biomass, and therefore increased yield. The promoters used in the vector constructs of the present invention may be modified, if desired, to affect their control characteristics.

Tissue specific promoters may also be utilized in the present invention. An example of a tissue specific promoter is the promoter active in shoot meristems (Atanassova, et al., 1992, Plant J., 2:291). Other tissue specific promoters useful in transgenic plants, such as the cdc2a promoter and cyc07 promoter, will be known to those of skill in the art. (See for example, Ito, et al., 1994, Plant Mol. Biol., 24:863; Martinez, et al., 1992, Proc. Natl. Acad. Sci. USA, 89:7360; Medford, et al., 1991, Plant Cell, 3:359; Terada, et al., 1993, Plant Journal, 3:241; Wissenbach, et al., 1993, Plant Journal, 4:411). There are promoters known which limit expression to particular plant parts or in response to particular stimuli (e.g., the patatin promoters or the promoters for the large or small subunits of ADP glucose pyrophosphorylase). These promoters which limit expression, such as those that direct expression to roots, could be operably associated with RKN to direct expression primarily in the tuber. One skilled in the art will know of many such plant part-specific promoters which would be useful in the present invention.

Promoters used in the nucleic acid constructs of the present invention may be modified, if desired, to affect their control characteristics. For example, the CaMV 35S promoter may be ligated to the portion of the ssRUBISCO gene that represses the expression of ssRUBISCO in the absence of light, to create a promoter which is active in leaves but not in roots. The resulting chimeric promoter may be used as described herein. For purposes of this description, the phrase "CaMV 35S" promoter thus includes variations of CaMV 35S promoter, e.g., promoters derived by means of ligation with operator regions, random or controlled mutagenesis, etc. Furthermore, the promoters may be altered to contain multiple "enhancer sequences" to assist in elevating gene expression.

Alternatively, the promoters utilized may be selected to confer specific expression of RKN in response to disease such as fungal infection. The infection of plants by fungal pathogens activate defense-related or pathogenesis-related (PR) genes which encode (1) enzymes involved in phenyl-propanoid metabolism such as phenylalanine ammonia lyase, chalcone synthase, 4-coumarate coA ligase and coumaric acid 4-hydroxylase, (2) proteins that modify plant cell walls such as hydroxyproline-rich glycoproteins, glycine-rich proteins, and peroxidases, (3) enzymes, such as chitinases and glucanases, that degrade the fungal cell wall, (4) thaumatin-like proteins, or (5) proteins of as yet unknown function. The defense-related or PR genes have been isolated and characterized from a number of plant species. The promoters of these genes may be used to obtain expression of RKN in transgenic plants when such plants are challenged with a pathogen, particularly a fungal pathogen such as Pi. The particular promoter selected should be capable of causing sufficient expression of RKN to result in the production of an effective amount of polypeptide.

Optionally, a selectable marker may be associated with the nucleic acid sequence to be inserted. The term "marker" has been defined above. Preferably, the marker gene is an antibiotic resistance gene whereby the appropriate antibiotic can be used to select for transformed plant cells from among plant cells that are not transformed. Examples of suitable selectable markers include adenosine deaminase, dihydro-folate reductase, hygromycin-B-phosphotransferase, thymidine kinase, xanthine-guanine phospho-ribosyltransferase and amino-glycoside 3'-O-phosphotransferase II (kanamycin, neomycin and G418 resistance). Other suitable markers will be known to those of skill in the art.

Vector(s) employed in the present invention for transformation of plant cells comprise a nucleic acid sequence encoding RKN polypeptide. operably associated with a promoter. To effect a transformation process in accordance with the present invention, it is first necessary to construct a suitable vector and properly introduce it into the plant cell. Details of the construction of vectors utilized herein are known to those skilled in the art of plant genetic engineering.

RKN nucleic acid sequences utilized in the present invention can be introduced into plant cells using Ti plasmids of Agrobacterium tumefaciens, root-inducing (Ri) plasmids, and plant virus vectors. (For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9, and Horsch, et al., 1985, Science, 227:1229, both incorporated herein by reference). In addition to plant transformation vectors derived from the Ti or root-inducing (Ri) plasmids of Agrobacterium, alternative methods of transformation may be utilized including the use of liposomes, electroporation, chemicals that increase free nucleic acid uptake, transformation using viruses or pollen and the use of biolistic transformation.

One of skill in the art will be able to select an appropriate vector for introducing the RKN polynucleotide sequence in a relatively intact state. Thus, any vector which will produce a plant carrying the introduced nucleic acid sequence should be sufficient. Even use of a naked piece of nucleic acid would be expected to confer the properties of this invention, though at low efficiency. The selection of the vector, or whether to use a vector, is typically guided by the method of transformation selected.

The transformation of plants in accordance with the invention may be carried out in essentially any of the various ways known to those skilled in the art of plant molecular biology. (See, for example, Methods of Enzymology, Vol. 153, 1987, Wu and Grossman, Eds., Academic Press, incorporated herein by reference). As used herein, the term "transformation" means alteration of the genotype of a host plant by the introduction of RKN nucleic acid sequence.

For example, an RKN nucleic acid sequence can be introduced into a plant cell utilizing *Agrobacterium tumefaciens* containing the Ti plasmid, as mentioned briefly above. In using an A. tumefaciens culture as a transformation vehicle, it is advantageous to use a nononcogenic strain of Agrobacterium as the vector carrier so that normal nononcogenic differentiation of the transformed tissues is possible. It is also preferred that the Agrobacterium harbor a binary Ti plasmid system. Such a binary system comprises I) a first Ti plasmid having a virulence region essential for the introduction of transfer nucleic acid (T-DNA) into plants, and 2) a chimeric plasmid. The latter contains at least one border region of the T-DNA region of a wild-type Ti plasmid flanking the nucleic acid to be transferred. Binary Ti plasmid systems have been shown effective to transform plant cells (De Framond, 1983, Biotechnology, 1:262; Hoekema, et al., 1983, Nature, 303:179). Such a binary system is preferred because it does not require integration into the Ti plasmid of Agrobacterium, which is an older methodology.

Methods involving the use of Agrobacterium in transformation according to the present invention include, but are not limited to: 1) cocultivation of Agrobacterium with cultured isolated protoplasts; 2) transformation of plant cells or tissues with Agrobacterium; or 3) transformation of seeds, apices or meristems with Agrobacterium.

In addition, gene transfer can be accomplished by in planta transformation by Agrobacterium, as described by Bechtold, et al., (1993, C.R. Acad. Sci. Paris, 316:1194) and exemplified in the Examples herein. This approach is based on the vacuum infiltration or dipping of a suspension of Agrobacterium cells.

The preferred method of introducing RKN polynucleotide into plant cells is to infect such plant cells, an explant, a meristem or a seed, with transformed *Agrobacterium tumefaciens* as described above. Under appropriate conditions known in the art, the transformed plant cells are grown to form shoots, roots, and develop further into plants.

Alternatively, RKN polynucleotide can be introduced into a plant cell using mechanical or chemical means. For example, the nucleic acid can be mechanically transferred into the plant cell by microinjection using a micropipette. Alternatively, the nucleic acid may be transferred into the plant cell by using polyethylene glycol which forms a precipitation complex with genetic material that is taken up by the cell.

RKN polynucleotide can also be introduced into plant cells by electroporation (Fromm, et al., 1985, Proc. Natl. Acad. Sci., U.S.A., 82:5824, which is incorporated herein by reference). In this technique, plant protoplasts are electroporated in the presence of vectors or nucleic acids containing the relevant nucleic acid sequences. Electrical impulses of high field strength reversibly permeabilize membranes allowing the introduction of nucleic acids. Electroporated plant protoplasts reform the cell wall, divide and form a plant callus. Selection of the transformed plant cells with the transformed gene can be accomplished using phenotypic markers as described herein.

Another method for introducing RKN polynucleotide into a plant cell is high velocity ballistic penetration by small particles with the nucleic acid to be introduced contained either within the matrix of such particles, or on the surface thereof (Klein, et al., 1987, Nature 327:70). Bombardment transformation methods are also described in Sanford, et al. (1991, Techniques 3:3–16) and Klein, et al. (1992, Bio/Techniques 10:286). Although, typically only a single introduction of a new nucleic acid sequence is required, this method particularly provides for multiple introductions.

Cauliflower mosaic virus (CaMV) may also be used as a vector for introducing nucleic acid into plant cells (U.S. Pat. No. 4,407,956). CaMV viral nucleic acid genome is inserted into a parent bacterial plasmid creating a recombinant nucleic acid molecule which can be propagated in bacteria. After cloning, the recombinant plasmid again may be cloned and further modified by introduction of the desired nucleic acid sequence (e.g., the RKN sequence). The modified viral portion of the recombinant plasmid is then excised from the parent bacterial plasmid, and used to inoculate the plant cells or plants.

As used herein, the term "contacting" refers to any means of introducing RKN into the plant cell, including chemical and physical means as described above. Preferably, contacting refers to introducing the nucleic acid or vector into plant cells (including an explant, a meristem or a seed), via *Agrobacterium tumefaciens* transformed with the RKN encoding nucleic acid as described above.

Normally, a transformed plant cell is regenerated to obtain a whole plant from the transformation process. The immediate product of the transformation is referred to as a "transgenote". The term "growing" or "regeneration" as used herein means growing a whole plant from a plant cell, a group of plant cells, a plant part (including seeds), or a plant piece (e.g., from a protoplast, callus, or tissue part).

Regeneration from protoplasts varies from species to species, but generally the process is initiated by first providing a suspension of protoplasts. In certain species, plant formation can be induced from the protoplast suspension, followed by ripening and germination as natural plant. The culture media will generally contain various amino acids and hormones, necessary for growth and regeneration. Examples of hormones utilized include auxins and cytokinins. It is sometimes advantageous to add glutamic acid and proline to the medium, especially for plant species such as corn and alfalfa. Efficient regeneration will depend on the medium, the genotype, and the history of the culture. If these variables are controlled, regeneration is reproducible.

Regeneration also occurs from plant callus, explants, organs or parts. Transformation can be performed in the context of organ or plant part regeneration. (see Methods in Enzymology, 1987, Vol. 118, and Klee, et al., 1987, Annual Review of Plant Physiology, 38:467). Utilizing the leaf disk-transformation-regeneration method of Horsch, et al., 1985, Science, 227:1229, disks are cultured on selective media, followed by shoot formation in about 2–4 weeks. Shoots that develop are excised from calli and transplanted to appropriate root-inducing selective medium. Rooted plantlets are transplanted to soil as soon as possible after roots appear. The plantlets can be repotted as required, until reaching maturity.

In vegetatively propagated crops, the mature transgenic plants are propagated by utilizing cuttings or tissue culture techniques to produce multiple identical plants. Selection of desirable transgyenotes is made and new varieties are obtained and propagated vegetatively for commercial use.

In seed propagated crops, the mature transgenic plants is self crossed to produce a homozygous inbred plant. The resulting inbred plant produces seed containing the newly introduced foreign gene(s). These seeds can be grown to produce plants that would produce the selected phenotype, e.g., increased yield.

Parts obtained from regenerated plant, such as flowers, seeds, leaves, branches, roots, fruit, and the like are included in the invention, provided that these parts comprise cells that have been transformed as described. Progeny and variants, and mutants of the regenerated plants are also included within the scope of the invention, provided that these parts comprise the introduced nucleic acid sequences.

Plants exhibiting increased yield or biomass as compared with wild-type plants can be selected by visual observation. In a preferred embodiment of the invention, the increased yield is a result of increased root production. This increased root production may of particular importance for growth in dry, arid areas, such as dessert conditions, or in areas with a limited water supply, such as areas under drought conditions. The invention includes plants produced by the method of the invention, as well as plant tissue and seeds.

In yet another embodiment, the invention provides a method for producing a genetically modified plant characterized as having increased yield as compared with a wild-type plant. The method includes introducing at least one nucleic acid sequence encoding RKN polypeptide into a plant cell to obtain a transformed plant cell; growing the transformed plant cell under conditions which allow expression of RKN polypeptide to obtain a plant having increased yield. Conditions such as environmental and promoter inducing conditions vary from species to species, but should be the same within a species.

In another embodiment, the invention provides a method of producing a plant characterized as having increased yield by contacting a susceptible plant with an RKN promoter-inducing amount of an agent which induces RKN gene expression, wherein induction of RKN gene expression results in production of a plant having increased yield as compared to a plant not contacted with the agent.

A "susceptible plant" refers to a plant that can be induced to utilize its endogenous RKN gene to achieve increased yield. The term "promoter inducing amount" refers to that amount of agent necessary to elevate RKN gene expression above RKN expression in a plant cell not contacted with the agent. For example, a transcription factor or a chemical agent may be used to elevate gene expression from RKN native promoter. Alternatively, RKN promoter may be a heterologous promoter susceptible to induction. The invention method envisions contacting cells containing endogenous RKN promoter or recombinantly produced RKN promoter.

In another embodiment, the invention provides a method for producing a genetically modified plant characterized as having increased expression of a gene product of interest in its roots as compared to a plant which has not been genetically modified (e.g., a wild-type plant) by introducing at least one nucleic acid sequence encoding a gene product of interest into a plant cell to obtain a transformed plant cell, wherein the nucleic acid sequence of interest is operably associated with an RKN expression control sequence. A plant is produced from the transformed plant cell under conditions which allow expression of the gene product of interest in the roots of the plant.

"Gene product of interest" is defined above. Gene products of interest include, but are not limited to polypeptides conferring resistance to a pathogen. A "pathogen" is a specific biological causative agent. Plant pathogens include bacteria, viruses, fungi, nematodes, and insects. An example of an agent which confers resistance to a pathogen is a antibiotic, which confers resistance to a bacteria, or an antifungal agent, which confers resistance to a fungus. Suitable genes of interest which confer resistance to pathogenic agents of plants are well known to one of skill in the art. Examples of genes of use with the subject invention are the MiAMP, which inhibits the growth of a variety of fungal, oomycete, and bacterial pathogens (Marcus, J. P. et al., 1997, Eur. J. Biochem. 244:743–9); Nramp or OsNramp1, which may provide resistance to bacterial infections (Belouchi, A., et al., 1995, Plant Mol. Biol. 29:1181–1196); Pto, which confers resistance to *Pseudomonas syringae* in tomato (Martin, G. G., et al., 1993, Science 262:1432–1436); and rat 2-5A synthetase which confers resistance to plant viruses PVS, PVX, and PVY (Truve, E., et al., 1994, Arch. Virol. Suppl. 9:41–50). Optionally, a selectable marker may also be associated with the nucleic acid sequence to be inserted.

The above disclosure generally describes the present invention. A more complete understanding can be obtained by reference to the following specific examples which are provided herein for purposes of illustration only and are not intended to limit the scope of the invention.

EXAMPLE 1

CLONING OF THE RKN GENE

1. Rice BAC Library Screening

The cloning strategy used for cloning the RKN gene is diagramed in FIG. 1. A 1130 bp fragment of rice cDNA clone containing 9 imperfect LRRs was used as probe to screen rice BAC library (kindly provided by Tom Holsten, Department of Plant Pathology, University of California, Davis (for description, see Wang et al., 1995)). The hybridization conditions used for BAC screening was followed the provider's protocol, summarized herein. Ten pieces of membrane separated by mesh screens were prehybridized in 100 ml prehybridization solution (7% SDS, 0.5 $Na_2PO_4$, pH=7.2, 1 mM EDTA) for at least 2 hours at 65° C. A probe was prepared using random labeling, denatured, and added to the solution. Hybridization was carried out overnight at 65° C. The hybridized membranes were rinsed briefly at room temperature in 500 ml washing solution (40 mM $Na_2PO_4$, pH=7.2, 0.1% SDS) and then washed at 65° C. for 10–20 min. The membranes were exposed to X-film. Colonies identified as positive were then requested from the University of California, Davis.

2. RKN Gene Cloning and Sequencing from BAC Clone

The plasmids were prepared from BAC clones using procedures routine in the art (see Maniatis 1989). Plasmid DNA was isolated and subjection to restriction digests using several different restriction enzymes. The resulting products were separated by agarose gel electrophoresis, and hybridized to cLRR probe (a Southern blot analysis). Overlapping bands which hybridized with the probe were isolated and cloned into pBluescript KS(−) vector (Strategene, La Jolla, Calif.). Subcloning was confirmed by Southern blot analysis with the cLRR probe. A 3.5 kb BamHI fragment and a 5.0 kb HindIII fragment were finally isolated and subcloned into pBluescript KS(−) from the BAC clone. These two fragments were sequenced either by creating sets of nested deletions (Ausubel et al., 1987) or by synthetic oligonucleotide walking, and the end sequences of their derivative clones were determined by the dideoxy chain-termination method (Sanger et al., 1977; Del Sal et al., 1989) using the DNA sequence kit version 2.0 (USB Corporation, Cleveland, Ohio). The primary sequencing data were analyzed using the LaserGene programs (DNASTAR Inc., Madison, Wis.). The polynucleotide sequence of the RKN gene (SEQ ID NO:1) is shown in FIG. 2. The deduced amino acid sequence (SEQ ID NO:2) is shown in FIG. 4. Database searches were performed using the U.S. National Center for Biotechnology Information with the BLAST program (Altschul et al., 1990) and the ALOM (Klein et al., 1985) was used in analyzing amino acid sequences for potential peripheral and membrane-spanning regions (FIGS. 3 and 5). Homologous proteins were also identified (FIGS. 6 and 7)

Results

1. Isolation and Sequencing of RKN Gene

Five positive BAC clones with an average DNA insert size of 125 kb were isolated using a 1130 bp fragment of rice CDNA clone containing 9 imperfect LRRs as probe to screen a rice BAC library from U.C. Davis (Wang et al., 1995). This probe was further used in Southern blot analyses of the five BAC clones digested with EcoRI, BamHI, HindIII and NotI. Several fragments corresponding to the bands hybridized to the probe were isolated, subcloned and sequenced. DNA sequence analysis indicated that a 4804 bp HindII fragment encodes a new leucine-rich repeat receptor kinase-like protein, designated RKN gene. The RKN gene has a single, large open reading frame of 2979 base pairs (FIG. 2), interrupted by one intron of 243 base pairs, coding for a polypeptide of 993 amino acids with a predicted molecular mass 105.4 kDa. It contains a 1196 bp 5' untranslated region and a 386 bp 3' untranslated region.

2. RKN Encodes a Putative Leucine-Rich Repeat/Receptor Protein Kinase, Similar to Various Receptor Protein Kinase in Plant The predicted 993 amino acid sequence of RKN gene (FIG. 4) revealed typical structure of a family of proteins called leucine-rich repeat (LRR) receptor kinase (FIG. 3). It has a 23-amino acid hydrophobic segment that presumably functions as a signal peptide to translocate the newly synthesized polypeptide into ER membrane (van Heijne, 1990) followed by a 43-amino acid which might be involved in forming homo- or heterodimers. Amino acid 75 to 615 constitutes the major extracellular domain which contained 22 imperfect copies of a 24-amino acid leucine-rich repeat (LRR) with 10 potential N-glycosylation sites (N-X-T/S) that are flanked by pairs of conservatively spaced cysteines. There is also a predicted transmembrane domain (amino acid 619–636) in RKN gene flanked by two stop-transfer sequences that are rich in charged amino acids. The sequence encoded by amino acids 660–993 contains a putative intracellular protein kinase catalytic domain. This region contains all 11 subdomain and all invariant amino acid residues found in almost all eukaryotic protein kineses. The sequences of HRDIKPSN in subdomain VI and GSCGYIAPE in subdomain VIII are strong indicators that it functions as a serine/threonine kinase rather than a tyrosine kinase (Hanks and Quinn, 1991).

3. RKN is a Single Copy Gene in Rice

A 1.15 kb BamHI/XbaI DNA fragment from RKN covering LRR 20–22, transmembrane domain and kinase subdomain I-VIII (amino acid 528–874) was isolated and used as probe to determine the copy number of the RKN gene in rice genome. The rice genome of Taipei 309 was digested with four different restriction enzymes (HindIII, XbaI, EcoRI and BamHI) and Southern blotted with the probe under high-stringency hybridization condition. Only a single band was detected in each lane. The single band appeared exacted at the 4.8 kb size in the lane digested with HindIII, which is in agreement with the predicted size of RKN gene. One restriction site of the other three restriction enzymes existed in the RKN gene. The Southern blot result suggest that the RKN gene is present as a single copy in rice genome.

EXAMPLE 2

RKN IS A FUNCTIONAL SERINE/THREONINE PROTEIN KINASE

Methods

1. Production of Mutants

The method used in this experiment was based on the protocol described by Sambrook et al. (1989) and modified by Qun Zhu (1995). Briefly, the target fragment was cloned into pBluescript (KS-) and transformed into dut-ung-*E. coli* strain RZ 1032 (Quantum Biotechnologies Inc., Quebec, Canada) to make single-strand DNA. The phosphorylated oligonucleotides containing appropriate mutations were annealed with the single-stranded DNA to synthesize the second-strand DNA using T4 DNA polymerase, and the gaps were repaired with T4 DNA ligase. The constructs containing mutations were confirmed by nucleotide sequence analysis.

2. Protein Expression and Purification

A DNA fragment encoding the whole kinase domain of RKN gene (without introns) was generated by in vitro mutagenesis and cloned between the EcoRV and XhoI sites of vector pET-29a in-frame with S-Tag and His-Tag (Novagen, Inc., Madison, Wis.). The vector contains a cleavable S-Tag sequence fused to N-terminal for rapid assay and a His-Tag sequence fused to C-terminal for rapid affinity purification. The resulting fusion construct called pETK was verified by DNA sequencing and transformed into bacterial BL21 (DE3) for expression of the S-Tag-Kinase-His-Tag fusion protein. A single colony from a freshly streaked plate was inoculated in 3 ml LB containing an appropriate antibiotic and incubated with shaking at 30° C. overnight. 1 ml of the overnight culture was then transferred into 50 ml LB containing the same antibiotic and continued the incubation. When the $OD_{600}$ reached 0.4–1, IPTG was added to a final concentration of 0.4 mM and the incubation was continued for an additional 3–4 hr. The cells were harvested by centrifugation at 5000× g for 5 min at 4° C. and resuspended in 0.2 culture volume of cold binding buffer (20 mM Tris-HCl, pH=7.9, 0.5 M NaCl, 5 mM imidazole) containing 0.5 mg lysozyme/ml. The cells were incubated in binding buffer on ice for 30 min., and then the sample was sonicated until it was no longer viscous. The lysate was centrifuged to remove the debris and the supernatant was filtered through a 0.45 micron membrane. The soluble proteins were then run over the His-Bind Resin using the manufacturer's protocol (pET System manual, Novagen Inc., Madison, Wis.).

The bound protein was eluted in elution buffer (20 mM Tris-HCl, pH=7.9, 0.5 M NaCl, 1 M imidazole) and collected in 1 ml aliquots. The concentration of the crude protein extract or the purified protein were measured by Bio-Rad Protein Assay Kit or run the SDS-polyacrylamide gel (SDS-PAGE).

3. Western Blot Assay

The crude or purified protein was fractioned using 12% SDS-PAGE gel electrophoresis and transferred onto PVDF membrane using a standard Western blotting protocol (Sambrook, 1989). S-Tag fusion protein expression was then analyzed using S-protein HIRP Conjugate (Novagen Inc., product 69047-1), which is highly specific for S-Tag fusion proteins. The SuperSignal CL-HRP substrate kit is was used following the manufacture's protocol (Novagen, Inc.) for the chemiluminescent detection of the S-protein HRP conjugate.

4. Autophosphorylation Protein Kinase Assay

About 1–5 μg protein was used in each reaction for kinase activity analysis Kinase activity analysis was carried out in an assay mixture containing 10 mM Tris-HCl, pH=7.0, 0.35 mM DTT, 10 mM $MgCl_2$. 10 μCi-ATP in a volume of 30 μl. The mixture was incubated for 30 min at 30° C. The reaction were stopped by the addition of SDS-PAGE sample buffer and fractionated in a 12% SDS-polyacrylamide gel. The radioactive gel was then subjected to autoradiography.

Results

To determine whether RKN encodes a functional protein kinase, the whole kinase domain including the intron was cloned into pBluescript. The intron inside the subdomain VIII was then deleted by insertion of two SmaI sites at the splicing position, and the splicing site was further mutated back to CCAGAG, the original sequence by site-directed mutagenesis. The kinase domain containing all the 11 subdomains without introns was finally fused in-frame with S-Tag and His-Tag between the EcoRV and XhoI sites of vector pET-29a and expressed in *E. coli* BL21 (DE3). The fusion protein was detected by S-protein HRP Conjugate on 12% SDS-PAGE gel and shown to have the expected molecular mass of 41 kDa. The fusion protein was expressed at minimal levels without IPTG induction. The expression level was increased if the culture was incubated at room temperature under 0.4 mM IPTG induction. The fusion protein was affinity purified and the purified protein band was visible in 12% SDS-PAGE stained by Commassie blue. Incubation of the purified fusion protein with ($^{32}$P) ATP in an in vitro kinase assay showed an autophosphorylation band appearing at around 41 kDa, suggesting that the kinase was capable of strong autophosphorylation. There was no autophosphorylation function when using $NaHPO_4$ buffer instead of Tris buffer in the kinase assay reaction.

EXAMPLE 3

FUNCTIONAL ANALYSIS IN TRANSGENIC PLANTS

Methods

1. Production of Transgenic Plants

Transgenic plants were generated as shown in FIG. 9 using the constructs illustrated in FIG. 10. Standard methods were used to obtain the transgenic plants.

2. Gus Activity Assay

Root, stem and leaf tissues of transgenic seedling plants were extracted separately in GUS extraction buffer (50 mM $NaPO_4$ pH=7.0, 10 mM beta-Mercaptoethanol. 10 mM Na EDTA, 0.1% Sodium Lauryl Sarcosine, 0.1% Triton X-100). GUS activity was assayed by fluorimetric determination of the production of 4-methylumbelliferone from the corresponding β-glucuronide followed the Fluorogenic Assay Protocol described in Jefferson, R. A. (1987). Protein concentration was determined by the method of Bradford (1976) and GUS activity was expressed as pmol of product per min. per mg. of protein.

Results

1. Constructs

In order to analyze the function of RKN gene in rice, several constructs were made to transform Taipei 309 to study the function of RKN in transgenic rice. Two fragments containing 5' untranslated region and N-terminal 70 and 84 amino acid (−1033 to +373 and −1033 to +415) were obtained by restriction enzymes digestion of HindIII/XmaI and HindIII/HincII, respectively. These two fragment were fused to HindIII/SmaI sites of pBI101.3 (Jefferson, R. A., 1987) separately to get in-frame RKN promoter::GUS gene fusion 1 and 2. These two RKN promoter::GUS gene fusion were used to study the promoter function in transgenic rice by testing the GUS activity. In order to overexpress the RKN gene in transgenic rice, the −90 to −800 enhancer region of the CaMV 35S promoter was inserted into a BgIII site placed −166 upstream of the transcription site of RKN gene to give 35S::RKN gene fusion.

2. RKN Promoter::Gus Fusion Activity Assay in Transgenic Rice

Figure 13:
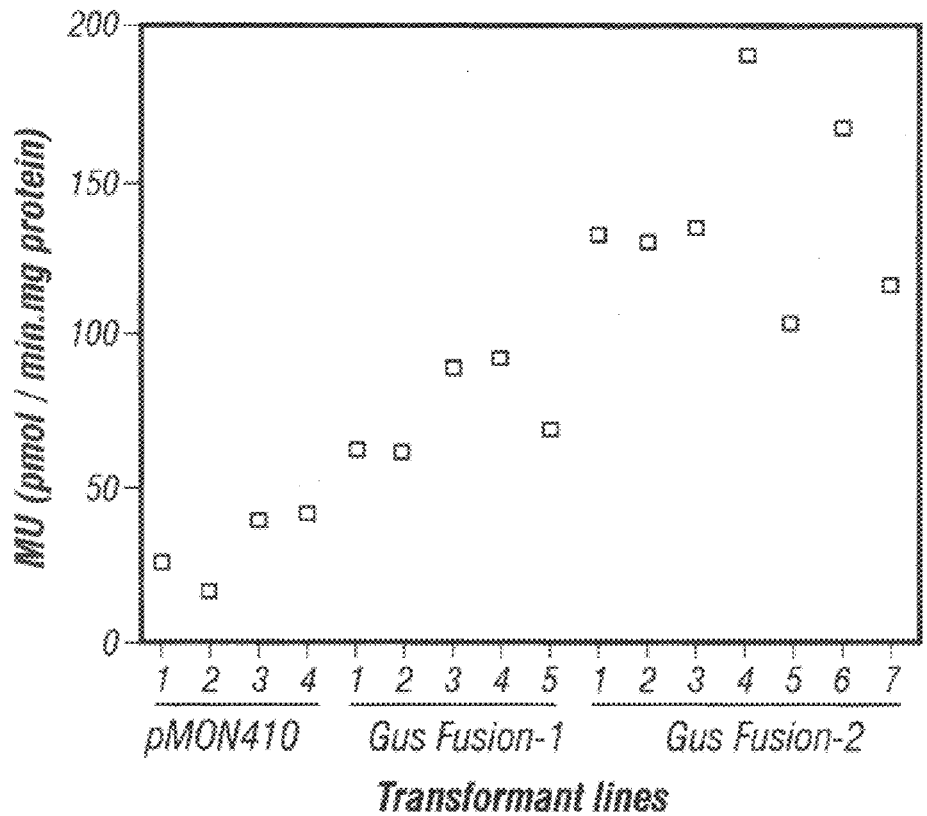
FIG. 13 shows RKN promoter::GUS fusion activity in roots isolated from three transformant lines.
Figure 14:
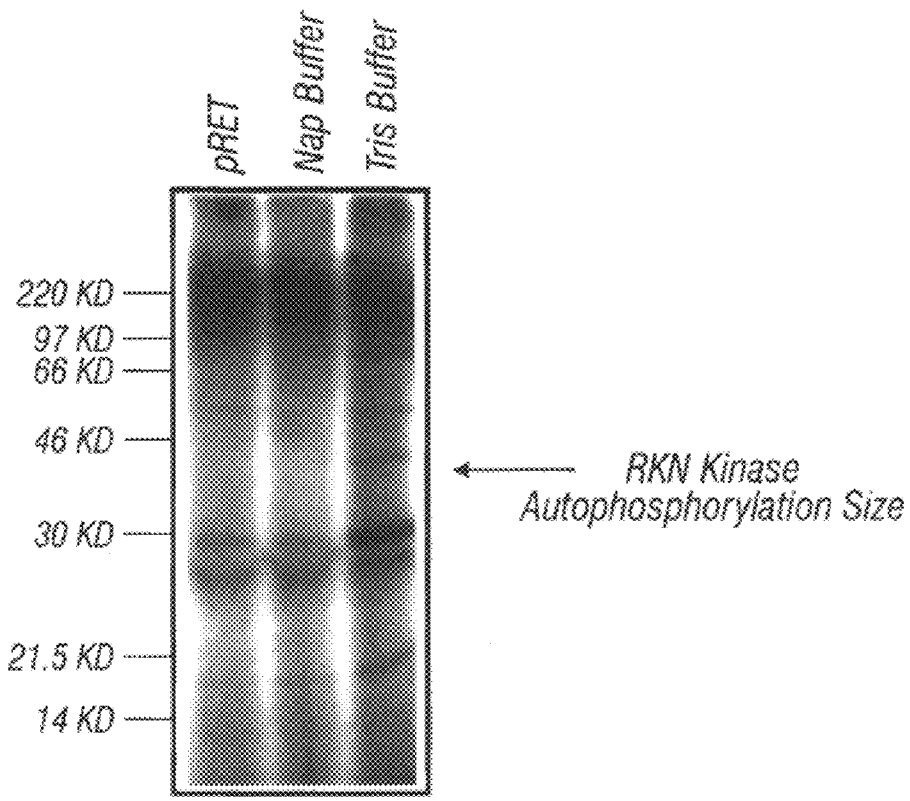
FIG. 14 shows RKN kinase autophosphorylation.

The 5'-flanking regions of the rice RKN gene (−1033 to +373 and −1033 to +415) was fused to the coding region of the GUS gene linked to the terminator of the nopaline synthase gene in order to specifically determine the expression pattern of the RKN gene. The gene fusions were cotransferred into the Taipei 309 rice genome with a plasmid pMON410 containing the hygromycin phosphotransferase gene using a biolistic method. (Methods of Enzymology, 1987, supra) pMON410 transformed into rice genome alone was used as control. There were several independent lines of hygromycin resistant calli regenerated in each of these transformations. Roots, stems and leaves from the transgenic seedlings were extracted separately and quantitatively analyzed for the GUS activity. The results showed there was no difference between stem, the GUS activity between leaf, the control and the two other gene fusion transformants. However, gene fusion 2 had six times more GUS activities and gene fusion 1 had three times more activities than the control lines as shown in FIG. 13 which suggests the RKN gene is functional in the roots of the plant.

3. Expression Pattern of 35S::RKN Gene in Rice

Figure 11:
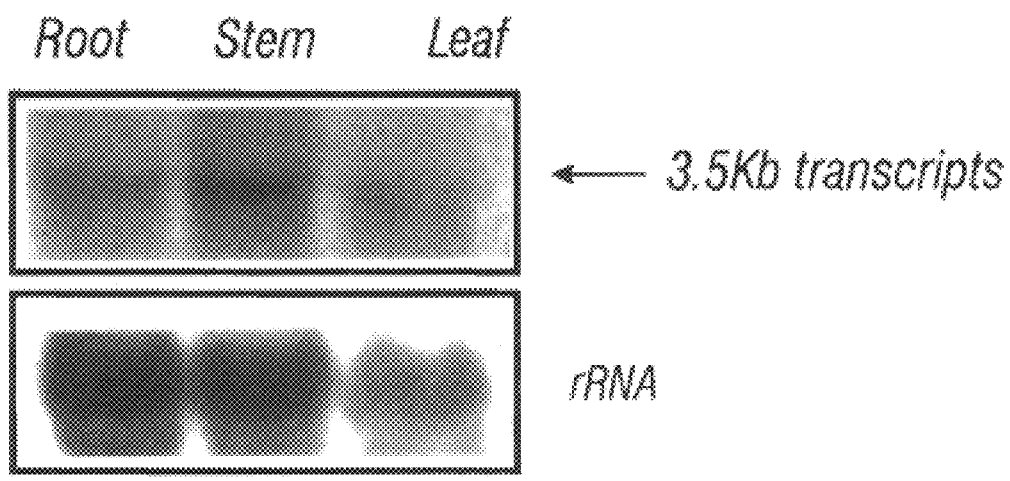
FIG. 11 shows a Northern blot of RNA extracted from seedlings of 35S::RKN transformants.

The 35S::RKN gene fusion containing the −90 to −800 enhancer region of the CaMV 35S promoter placed −166 upstream of the transcription site of RKN gene and the whole RKN coding region was cotransferred into the Taipei 309 rice genome with pMON410 using a biolistic method and regenerated. The RNA from the root, stem and leaf organs of transgenic seedling and wild type Taipei 309 seedling were extracted and the RKN gene transcripts accumulation was monitored by Northern blot assay (see FIG. 11). The 1.15 kb BamHI/XbaI fragment from RKN covering LRR 20–22, transmembrane domain and kinase subdomain I-VIII. (amino acid 528–874) was used for Southern blotting and in the Northern hybridization. The transcripts were hardly detected in wild type rice, but full length 3.5 kb transcripts of RKN gene were demonstrated in RNA extracted from the 35S::RKN transgenic rice. The RNA expression levels of RKN gene from different organs (leaf, stem and root) were almost the same in the 35S::RKN transgenic rice.

EXAMPLE 4

TRANSCRIPTION AND TRANSLATION START SITE METHODS

1. Primer Extension Assay

A 26-mer oligonucleotide RKN-PE 5' GGAGGAGTC-GAAGGGAGGAGATGGCC 3' (SEQ ID NO:4) which was complementary to nucleotides 35 bp upstream of the putative translation start site ATG was synthesized. The 5' terminus of RKN-PE was labeled with 32P-ATP by T4 polynucleotide kinase (Sambrook et al., 1989) for primer extension analyses. 30 µg total RNA prepared from seedling samples of 35S::RKN gene fusion transformants, air dried, and resuspended in 7 µl sterile TE buffer (10 mM Tris-HCl. pH=8.3, 1 mM EDTA). 1 µl of labeled RKN-PE primer (about $7\times10^{-3}$ pmol), 2 µl 5× annealing buffer (10 mM Tris-HCl, pH=8.3, 1 mM EDTA, 1.25 M KCl) were then added. After annealing for 30 min at 55° C., the annealing mixture were briefly microcentrifuged and annealed for another 30 min. at 55° C. Following the second annealing, 23 µl of extension solution containing 20 mM Tris-HCl, pH=8.3, 10 mM $MgCl_2$, 100 µg/ml actinomycin D, 5 mM DTT, 0.33 mM dNTPs and 10 units of avian myeloblastosis virus (AMV) reverse transcriptase (Life Science, Inc., Florida) was then added to the mixture. After incubation at 37–39° C. for 1 hr, primer extension products were precipitated using 300 µl 100% EtOH containing 0.5 M NH4-acetate. After microcentrifuging for 15 min at 4° C., pellets were washed with 70% EtOH before vacuum drying. The dried pellet was well resuspended in 8 µl 100% formamide, and then mixed with 2 µl loading buffer (85% formamide, 10 mM NaOH, 0.05% bromophenol blue, 0.05% xylene cylanol). The entire sample was separated on a 8% sequencing gel (Sambrook et al., 1989). During this process, a sequence reaction was made using the corresponding primer (Oligo RKN-PE) and template (RKN plasmid) by the dideoxy chain-termination method, and loaded on the sequencing gel at the same time as the primer extension (used as reference). Radioactive products were detected by autoradiography with XAR-film (Kodak).

Results

The RNA isolated from different organs of 35S::RKN transgenic seedlings was used to determine the transcription start site by primer extension analysis. A 26-mer oligonucleotide identical to the sequence of the antisense DNA strand at the residues 69–42 downstream from the first ATG was synthesized and used in the primer extension assay. One major product was obtained in all of samples (100 nucleotides in length) which corresponded to the position of the second "A" in the direct repeat sequence ATGGCCATG-GCC (SEQ ID NO:5). This position was designated as +1. There are two putative translation initiation codons (ATG) with a 105 bp distance between them. Both are in the same reading frame, and both of them have a purine (G) at −3 bp position upstream of the ATG which was a favorable context for initiating translation in eukaryotes (Kozak, 1989). However, the hydrophobicity plot showed the second ATG is mostly like the initiating translation codon because the NH,-terminus from the second ATG encodes 23 hydrophobic residues which are the characteristic of a signal peptide (von Heijie, 1990).

EXAMPLE 5

PHENOTYPE OF 35S::RKN GENE FUSION TRANSGENIC RICE: INCREASED ROOT GROWTH RATE IN TRANSGENIC PLANTS

Methods

Transgenic plants were obtained as described above. Dried mature seeds were immersed in water for 2–3 days at RT and then incubated in 37° C. overnight for germination. Germinated seeds were transferred to a membrane growing on the surface of water in a water container at 28° C. under 16 hr light/8 hr dark cycle. The root lengths were measured every other day.

Results

The particle bombardment method was used in this experiment to produce the transgenic rice carrying the 35S::RKN gene fusion. The success of this method is depended on the calli regeneration efficiency. The bombardment materials were grown on selection medium and pre-regeneration medium subsequently before being transferred to regeneration medium. Generally, the calli regenerated to get shoots in two to four weeks on regeneration medium, and then produced roots when the regenerated shoots were transferred to ½ MS medium (Li, 1993).

The 35S::RKN gene fusion construct was cotransformed into rice calli with pMON410 and the calli regenerated as the normal procedure. Calli transformed with pMON alone was used as a control. When the calli transformed with 35S::RKN gene fusion construct were transferred to regeneration medium, the calli regenerated very fast compared to the control (see FIG. 12). The regenerated shoots were initiated in one week as compared to two to four weeks for controls. Furthermore, the calli containing the 35S::RKN gene fusion produced roots quickly which grew very fast and strong in the regeneration medium. The experiment repeated twice and the phenotype was the same in each experiment. The results showed that the overexpression of RKN gene the rice can enhance the root production and calli regeneration.

Although the invention has been described with reference to the presently preferred embodiments, it should be understood that various modifications can be made without departing from the spirit of the invention. Accordingly, the invention is limited only by the following claims.

What is claimed is:

1. An isolated polynucleotide encoding a receptor-like protein kinase (RKN) polypeptide, wherein said polynucleotide hybridizes to a polynucleotide encoding SEQ ID NO: 2 under high stringency conditions and whereby said RKN polypeptide has a receptor protein kinase activity of the amino acid sequence as set forth in SEQ ID NO: 2.

2. An isolated polynucleotide encoding a receptor-like protein kinase (RKN) polypeptide comprising the amino acid sequence as set forth in SEQ ID NO: 2.

3. The polynucleotide of claim 1, comprising the nucleotide sequence as set forth in SEQ ID NO: 1.

4. An isolated polynucleotide selected from the group consisting of:
  a) SEQ ID NO: 1;
  b) a ribonucleotide sequence complementary to SEQ ID NO: 1, wherein T is U;
  c) nucleic acid sequences complementary to the polynucleotides of a) and b); and
  d) fragments of a), b), or c) that are at least 15 bases in length and that hybridize to DNA which encodes RKN as set forth in SEQ ID NO: 2.

5. The polynucleotide of claim 1, wherein said polynucleotide is operatively linked to an expression control sequence.

6. The polynucleotide of claim 5, wherein the expression control sequence is a promoter.

7. The polynucleotide of claim 6, wherein the promoter is tissue specific.

8. An expression vector containing the polynucleotide of claim 4.

9. The vector of claim 8, further comprising a selectable marker.

10. The vector of claim 9, wherein said selectable marker confers antibiotic resistance.

11. The vector of claim 8, wherein the vector is a viral vector.

12. The vector of claims 8, wherein the vector is a plasmid.

13. The vector of claim 12, wherein the plasmid is a Ti plasmid of *Agrobacterium tumefaciens*.

14. The vector of claim 12, wherein the plasmid is a Ri plasmid of *Agrobacterium tumefaciens*.

15. An isolated host cell containing the vector of claim 8.

16. A method of producing a genetically modified plant exhibiting increased growth and yield as compared to the corresponding wild-type plant, said method comprising:
  contacting plant cells with a polynucleotide of claim 1, wherein said polynucleotide is operatively associated with an expression control sequence, to obtain transformed plant cells;
  producing plants from said transformed plant cells under conditions which allow expression of the RKN polypeptide; and
  selecting a plant exhibiting said increased yield.

17. A The method of claim 16, wherein the genetically modified plant exhibits increased root growth.

18. The method of claim 16, wherein the expression control sequence is a promoter.

19. The method of claim 16, wherein the contacting is by physical means.

20. The method of claim 16, wherein the contacting is by chemical means.

21. The method of claim 16, wherein the plant cell is selected form the group consisting of protoplasts, gamete producing cells, and cells which regenerate into whole plants.

22. The method of claim 16, wherein said polynucleotide is contained in a T-DNA derived vector.

23. A plant produced by the method of claim 16.

24. Plant tissue derived from a plant produced by the method of claim 16.

25. A seed derived from a plant produced by the method of claim 16.

26. A method for genetically modifying a plant cell such that a plant, produced from said cell, exhibits modulated yield as compared with a wild-type plant, said method comprising:

introducing the RKN polynucleotide of claim 2 into a plant cell to obtain a transformed plant cell; and growing the transformed plant cell under conditions which permit modulation of the RKN polypeptide., thereby producing a plant that exhibits a modulated yield.

27. The method of claim 26, wherein said modulated yield is increased yield.

28. The method of claim 27, wherein said increased yield is achieved by augmenting expression of receptor-like protein kinase (RKN) in the plant.

29. An isolated polynucleotide having a nucleotide sequence selected from the group consisting of:

a) the deoxyribonucleotide sequence set forth as SEQ ID NO: 1;

b) a deoxyribonucleotide sequence complementary to the nucleotide sequence set forth as SEQ ID NO: 1; and c) a ribonucleotide sequence complementary to the nucleotide sequence set forth as SEQ ID NO: 1 or a nucleotide sequence complementary thereto.

30. An isolated polynucleotide consisting of at least 15 nucleotides that will hybridize to a nucleotide sequence selected from the group consisting of:

a) the nucleotide sequence set forth as SEQ ID NO: 1 or a nucleotide sequence complementary thereto; and b) a nucleotide sequence encoding the amino acid sequence as set forth in SEQ ID NO: 2 or a nucleotide sequence complementary thereto.

31. A host cell containing the vector of claim 8, provided said host cell is not a human host cell.

* * * * *

SEQUENCE LISTING

<160> NUMBER OF SEQ ID NOS: 8

<210> SEQ ID NO 1
<211> LENGTH: 4804
<212> TYPE: DNA
<213> ORGANISM: Oryza sp.

<400> SEQUENCE: 1

-continued

| | | | | |
|---|---|---|---|---|
| aagcttgtgt | atatgctcgt | tccaagctac | acatcatatt | ctcctcggaa aagggaactt | 60 |
| ataggttagt | aatcctatgc | acgccatcct | ttctttcagt | agaaacatgt gtaagatcgt | 120 |
| gatgtgaaag | taggtattaa | ataggtggg | attatctatc | ttttttgctt attccggagg | 180 |
| ttttttttga | atttcaatgg | ttggaattgg | agtgtttcac | atagaaattc ctttgttgca | 240 |
| atgaaaatgt | atctcattga | attcatatat | ttttaatgcc | caggctgact aagctagcag | 300 |
| catagcaaga | aaaggtaaca | gtactaatta | ggagaaactt | taccactctt aaagagatac | 360 |
| aaaattttc | taatgtaaaa | ttgggtaaag | gtgccaattt | ttactataca agatgtactt | 420 |
| ctaatacata | ggtcaaatta | ctaactagtt | aaactatgtt | tgaaacaccg gaaaaattac | 480 |
| tacttccctc | cattttatat | tataagttgt | tttaactttt | tttaagttga atttctttta | 540 |
| atttgatcaa | gtttataaaa | aaacatatta | gccaaaatat | atttaatgtt agatttaagg | 600 |
| aaactaattt | gatgtttgag | atgttactaa | attttaaac | tttgataaat caaaacactt | 660 |
| ataatatgaa | acggagaacc | cggagagata | gttcctacga | attttgattt ttttttttgac | 720 |
| aattccaaga | aaaccctat | gaaattcatg | ggttccaaaa | tctcttgaac caattgtgaa | 780 |
| tagagctttt | ttttttagaa | ctgtcaatta | acagagttaa | tggcattatc agatcacaga | 840 |
| gtaatatcat | agtctgtgta | aattcaagat | cttaatccat | attgatttga agtagcaaat | 900 |
| gcaaggaaca | aagaggagaa | gaagaaaaaa | aatggttggc | tgctgcaata gtgggatcac | 960 |
| cacccaaaac | catctctttc | caaagcgaag | ccgaccaccg | ccatcatggc cacctccacc | 1020 |
| tccacccatg | gccatggcca | tctcctccct | tcgactcctc | ctcctccccc ctccgacctc | 1080 |
| ctcatcatga | catgccgcag | ccacaatgta | ccaccaccgc | caccaccttt cccgcctcca | 1140 |
| ttttaccacc | acccctcct | cctcctcgca | ccacctccac | cacctccgcc accgccatgg | 1200 |
| ccgccgccgc | cgtccatgtc | ctgcttttgc | tgctgcctct | cgctaccatc acatccgcgt | 1260 |
| cgtcggcgcc | gctcccgctg | ctcgcgctgc | tgtcgctgag | gtcgtcgctg ggcgaccccg | 1320 |
| ccggcgcgct | gcggtcgtgg | acgtacgccg | cggcggcgtc | cgcgggcgcc accaggtcgc | 1380 |
| tggcgccgcc | gtggtgcgcg | tggcccgggg | tggcgtgcga | cggggcaacc ggggaggtcg | 1440 |
| tcggggtcga | cctgtcgcgg | cggaacctgt | ccggcaccgt | gtcgcccacc gccgcgaggc | 1500 |
| tgctgtcccc | gacgctgacg | tcgctgaacc | tcagcgggaa | cggttcgccg gcgagctccc | 1560 |
| gccgcgtgct | cctgctccgg | cggctcgtgg | cgcttgatgt | tagccataac ttcttcaact | 1620 |
| ccacgttccc | cgacggcatc | gccaagctcg | gcgggttcgc | cttccttgac gccttcagca | 1680 |
| actgcttcgt | cggggagctc | ccccgtggca | tcggcgagct | ccggaggctc gagcacctca | 1740 |
| acctcggtgg | cagcttcttc | aacgggagca | tccccgcga | ggtcgggcag ctgcggcggc | 1800 |
| tgcggtttct | gcacctcgcg | gggaaccgtc | tctccgggcg | gctgccgagg gagctcggcg | 1860 |
| agctcacgtc | ggtcgaacac | cttgagattg | gtacaatgc | gtacgacggc gggataccgg | 1920 |
| agttcgggaa | gatggcacag | ctccggtacc | tcgatatcgc | cgccgccaac gtgtccgggc | 1980 |
| ccgtgccgcc | ggagctcggc | ggactcacgc | ggcttgaatc | tctgttcctg ttcaagaaca | 2040 |
| ggatcggccg | gcgcgatccg | ccgcggtggt | ctcgcctccg | agcgctccag gttctcgacg | 2100 |
| tctcggacaa | ccacctcgcc | ggcgcgatcc | cggcgctcgg | cgagctcacc aacctcacga | 2160 |
| cgctgaatct | catgagcaac | tccctctccg | gcacgatccc | ggcggcgatc ggcgcgctgc | 2220 |
| cgagcctcga | ggtgctccag | ctatggaaca | actcgctcgc | cggaggctg ccggagtcgc | 2280 |
| tcggcgcgag | ccggcggctt | gtccggctcg | acgtgtcgac | gaactccctc tccggcccga | 2340 |
| ttcctcccgg | tgtctgcgcc | ggcaaccgcc | tcgcccgcct | catcctcttc gacaaccggt | 2400 |

```
tcgactccgc gattccggcg agcctcgccg actgctcgtc gctgtggcgc gtccggctcg    2460
aggcgaaccg gctctccggc gagattccag cggggttcgg cgcgatacgg aatctgacgt    2520
acatggactt gagctccaac tcgctcaccg gcggcggcat tccggccgac ctggtcgctt    2580
ctcccagcct tgagtacttc aacgtctccg gcaacctggt cggccggccg ctgccggaca    2640
tggcgtggcg ggggccgaag ctgcaggtgt tcgcggcgag cagatgcggt ctggtcggcg    2700
agctcccggc gttcggcgcc accgggtgcg cgaacctgta ccgcctagag ttggccggga    2760
acgcgctggg cggcgggatc cccggcgaca ttggcagctg caagcggctg gtgagcttga    2820
ggctgcagca caacgagctc accggagaga taccggcggc gatcgcgctg ccgtcgatca    2880
ccgaggtcga cctgtctgga acgcgctcac cggcaccgtc cgccggggtt caccaactgc    2940
acgacgtgga gacgttcgac gtgtcgttca accacctggc gccggccgag ccgtcgtcgg    3000
acgccggcga acgcggcagc ccgcgcggca cacggcggca atgtgggtgc cgccgtggc    3060 ggtgcgcgtt cgccggcatg gtggtgctcg cgggcaccgc gcgctggctg cagtggcgtg    3120
gcggcgacga cacggccgcg gcagacgcgc gcggtcccgg cggcgcgcgc caccccgacc    3180
tcgtcgtcgg gccgtggcgg atgaccgcgt tccagaggct gagcttcacc gccgacgacg    3240
tgccgaggtg cgtcgagggg agcgacggca tcgtcggcgc cgggtcgtcg gggacggtgt    3300
accgcgccaa gatgcccaat ggcgaggtca tcgccgtgaa gaagctgtgg caggcggcgg    3360
cgcagaagga ggcagccgca ccgacggagc agaaccagaa gctccggcaa gacagcgacg    3420
gcggcggcgg cggcaagagg acggtggccg aggtggaggt gctcggccac ctccgccacc    3480
gcaacatcgt ccggctgctg gggtggtgca ccaacggcga gtccacgatg ctgctctacg    3540
agtacatgcc caacggcagc ctcgacgagc tcctccacgc ccgcgccaag gcgccgcggg    3600
ctgggacgcc cggtacaaga tcgccgtcgg tcgcgcaggg cgtcagctac ctccaccacg    3660
actgcctccc cgccatcgcg caccgcgaca tcaagcccag caacatcctc tcgacgacga    3720
catggaggca cgcgctcgcc gacttcgcg tcgccaaggc gctccagagc gccgccccca    3780
tgtccgtcgt cgccggctca tgcggctaca ttgcaccagg tgagccgcat acacatcatc    3840
cgccacgtgt ccatcaaaat cattactaac tccgtttcat gttataagac tttctaacat    3900
tgcccacata tcatatatat gttaatgaat ctagacacat gcgtatctag attgtgtcta    3960
gattcattaa catatatatg aatgtgggta atactagaaa gtcttataat ataaaataga    4020
tgaaataatt aatcatattt tttatttttg tcatttccta agagtacacg tacactctaa    4080
aagtgaacga gaagagcgat gtgtacagct tcggtgtggt actattggag atcctgacgg    4140
gacggcggtc ggtggaggcg gagtacgggg aggggaacaa catcgtggac tgggtgcggc    4200
ggaaggtggc cggaggcggg gtgggcgacg tgatcgacgc tgcggcgtgg gccgacaatg    4260
atgtcggtgg cacgcgggac gagatggcgc tggcgttagg gtggcgctgc tgtcaccagc    4320
cggtgccgca ggagcggccg tcgatgaggg aggtgctgtc catgctgcag gaggccaggc    4380
cgaaacggaa gaactcggcc aagaagcagg ttaagtaaaa tgggtgatgg ttaagtcttt    4440
agcagaaaga agaactaata tatatggtgt gctcttcgtg tgcagtgtgt gttgtgtatg    4500
tataattaac ttatttagtt actgtcatga atgggcttgc atatttcttg agcaattttc    4560
gtgatgttat ttaagggtga attacatttg ctatacaaat cttgtttaa actgtgtaat    4620 tgtattcagt tatgatgacc aatgtacacc gttataattt agatatatca cgcgattaac    4680
atcttgttta ttgataagtt actcggatag cagtgaaacc taaggaaaat ttcaactgtg    4740
```

-continued

```
caacttctgc aaaaatgatc aatgtgctga aaatactaac ggcctccaac ttaatggtaa    4800
gctt                                                                 4804
```

<210> SEQ ID NO 2
<211> LENGTH: 1028
<212> TYPE: PRT
<213> ORGANISM: Oryza sp.

<400> SEQUENCE: 2

```
Met Pro Gln Pro Gln Cys Thr Thr Thr Ala Thr Thr Phe Pro Ala Ser
  1               5                  10                  15

Ile Leu Pro Pro Pro Pro Pro Arg Thr Thr Ser Thr Thr Ser
                 20                  25                  30

Ala Thr Ala Met Ala Ala Ala Val His Val Leu Leu Leu Leu
             35                  40                  45

Pro Leu Ala Thr Ile Thr Ser Ala Ser Ser Ala Pro Leu Pro Leu Leu
         50                  55                  60

Ala Leu Leu Ser Leu Arg Ser Ser Leu Gly Asp Pro Ala Gly Ala Leu
 65                  70                  75                  80

Arg Ser Trp Thr Tyr Ala Ala Ala Ser Ala Gly Ala Thr Arg Ser
                 85                  90                  95

Leu Ala Pro Pro Trp Cys Ala Trp Pro Gly Val Ala Cys Asp Gly Ala
            100                 105                 110

Thr Gly Glu Val Val Gly Val Asp Leu Ser Arg Arg Asn Leu Ser Gly
            115                 120                 125

Thr Val Ser Pro Thr Ala Ala Arg Leu Leu Ser Pro Thr Leu Thr Ser
        130                 135                 140

Leu Asn Leu Ser Gly Asn Gly Ser Pro Ala Ser Ser Arg Arg Val Leu
145                 150                 155                 160

Leu Leu Arg Arg Leu Val Ala Leu Asp Val Ser His Asn Phe Phe Asn
                165                 170                 175

Ser Thr Phe Pro Asp Gly Ile Ala Lys Leu Gly Gly Phe Ala Phe Leu
            180                 185                 190

Asp Ala Phe Ser Asn Cys Phe Val Gly Glu Leu Pro Arg Gly Ile Gly
            195                 200                 205

Glu Leu Arg Arg Leu Glu His Leu Asn Leu Gly Gly Ser Phe Phe Asn
        210                 215                 220

Gly Ser Ile Pro Gly Glu Val Gly Gln Leu Arg Arg Leu Arg Phe Leu
225                 230                 235                 240

His Leu Ala Gly Asn Arg Leu Ser Gly Arg Leu Pro Arg Glu Leu Gly
                245                 250                 255

Glu Leu Thr Ser Val Glu His Leu Glu Ile Gly Tyr Asn Ala Tyr Asp
            260                 265                 270

Gly Gly Ile Pro Glu Phe Gly Lys Met Ala Gln Leu Arg Tyr Leu Asp
            275                 280                 285

Ile Ala Ala Ala Asn Val Ser Gly Pro Val Pro Pro Glu Leu Gly Gly
        290                 295                 300

Leu Thr Arg Leu Glu Ser Leu Phe Leu Phe Lys Asn Arg Ile Gly Arg
305                 310                 315                 320

Arg Asp Pro Pro Arg Trp Ser Arg Leu Arg Ala Leu Gln Val Leu Asp
                325                 330                 335

Val Ser Asp Asn His Leu Ala Gly Ala Ile Pro Ala Leu Gly Glu Leu
            340                 345                 350

Thr Asn Leu Thr Thr Leu Asn Leu Met Ser Asn Ser Leu Ser Gly Thr
```

```
              355                 360                 365
Ile Pro Ala Ala Ile Gly Ala Leu Pro Ser Leu Glu Val Leu Gln Leu
370                 375                 380

Trp Asn Asn Ser Leu Ala Gly Arg Leu Pro Glu Ser Leu Gly Ala Ser
385                 390                 395                 400

Arg Arg Leu Val Arg Leu Asp Val Ser Thr Asn Ser Leu Ser Gly Pro
                405                 410                 415

Ile Pro Pro Gly Val Cys Ala Gly Asn Arg Leu Ala Arg Leu Ile Leu
                420                 425                 430

Phe Asp Asn Arg Phe Asp Ser Ala Ile Pro Ala Ser Leu Ala Asp Cys
                435                 440                 445

Ser Ser Leu Trp Arg Val Arg Leu Glu Ala Asn Arg Leu Ser Gly Glu
                450                 455                 460

Ile Pro Ala Gly Phe Gly Ala Ile Arg Asn Leu Thr Tyr Met Asp Leu
465                 470                 475                 480

Ser Ser Asn Ser Leu Thr Gly Gly Ile Pro Ala Asp Leu Val Ala
                485                 490                 495

Ser Pro Ser Leu Glu Tyr Phe Asn Val Ser Gly Asn Leu Val Gly Arg
                500                 505                 510

Pro Leu Pro Asp Met Ala Trp Arg Gly Pro Lys Leu Gln Val Phe Ala
                515                 520                 525

Ala Ser Arg Cys Gly Leu Val Gly Glu Leu Pro Ala Phe Gly Ala Thr
                530                 535                 540

Gly Cys Ala Asn Leu Tyr Arg Leu Glu Leu Ala Gly Asn Ala Leu Gly
545                 550                 555                 560

Gly Gly Ile Pro Gly Asp Ile Gly Ser Cys Lys Arg Leu Val Ser Leu
                565                 570                 575

Arg Leu Gln His Asn Glu Leu Thr Gly Glu Ile Pro Ala Ala Ile Ala
                580                 585                 590

Leu Pro Ser Ile Thr Glu Val Asp Leu Ser Gly Thr Arg Ser Pro Ala
                595                 600                 605

Pro Ser Ala Gly Val His Gln Leu His Asp Val Glu Thr Phe Asp Val
                610                 615                 620

Ser Phe Asn His Leu Ala Pro Ala Glu Pro Ser Ser Asp Ala Gly Glu
625                 630                 635                 640

Arg Gly Ser Pro Arg Gly Thr Arg Arg Cys Gly Cys Pro Pro Trp
                645                 650                 655

Arg Cys Ala Phe Ala Gly Met Val Val Leu Ala Gly Thr Ala Arg Trp
                660                 665                 670

Leu Gln Trp Arg Gly Gly Asp Asp Thr Ala Ala Ala Asp Ala Arg Gly
                675                 680                 685

Pro Gly Gly Ala Arg His Pro Asp Leu Val Val Gly Pro Trp Arg Met
690                 695                 700

Thr Ala Phe Gln Arg Leu Ser Phe Thr Ala Asp Asp Val Pro Arg Cys
705                 710                 715                 720

Val Glu Gly Ser Asp Gly Ile Val Gly Ala Gly Ser Ser Gly Thr Val
                725                 730                 735

Tyr Arg Ala Lys Met Pro Asn Gly Glu Val Ile Ala Val Lys Lys Leu
                740                 745                 750

Trp Gln Ala Ala Ala Gln Lys Glu Ala Ala Pro Thr Glu Gln Asn
                755                 760                 765

Gln Lys Leu Arg Gln Asp Ser Asp Gly Gly Gly Lys Arg Thr
                770                 775                 780
```

Val Ala Glu Val Glu Val Leu Gly His Leu Arg His Arg Asn Ile Val
785                 790                 795                 800

Arg Leu Leu Gly Trp Cys Thr Asn Gly Glu Ser Thr Met Leu Leu Tyr
            805                 810                 815

Glu Tyr Met Pro Asn Gly Ser Leu Asp Glu Leu Leu His Ala Arg Ala
            820                 825                 830

Lys Ala Pro Arg Ala Gly Thr Pro Gly Thr Arg Ser Pro Ser Val Ala
            835                 840                 845

Gln Gly Val Ser Tyr Leu His His Asp Cys Leu Pro Ala Ile Ala His
850                 855                 860

Arg Asp Ile Lys Pro Ser Asn Ile Leu Ser Thr Thr Thr Trp Arg His
865                 870                 875                 880

Ala Leu Ala Asp Phe Gly Val Ala Lys Ala Leu Gln Ser Ala Ala Pro
            885                 890                 895

Met Ser Val Val Ala Gly Ser Cys Gly Tyr Ile Ala Pro Glu Tyr Thr
            900                 905                 910

Tyr Thr Leu Lys Val Asn Glu Lys Ser Asp Val Tyr Ser Phe Gly Val
            915                 920                 925

Val Leu Leu Glu Ile Leu Thr Gly Arg Arg Ser Val Glu Ala Glu Tyr
930                 935                 940

Gly Glu Gly Asn Asn Ile Val Asp Trp Val Arg Arg Lys Val Ala Gly
945                 950                 955                 960

Gly Gly Val Gly Asp Val Ile Asp Ala Ala Ala Trp Ala Asp Asn Asp
            965                 970                 975

Val Gly Gly Thr Arg Asp Glu Met Ala Leu Ala Leu Gly Trp Arg Cys
            980                 985                 990

Cys His Gln Pro Val Pro Gln Glu Arg Pro Ser Met Arg Glu Val Leu
            995                 1000                1005

Ser Met Leu Gln Glu Ala Arg Pro Lys Arg Lys Asn Ser Ala Lys Lys
    1010                1015                1020

Gln Val Lys Glx
1025

<210> SEQ ID NO 3
<211> LENGTH: 1091
<212> TYPE: DNA
<213> ORGANISM: Oryza sp.

<400> SEQUENCE: 3
aagcttgtgt atatgctcgt tccaagctac acatcatatt ctcctcggaa aagggaactt     60
ataggttagt aatcctatgc acgccatcct ttctttcagt agaaacatgt gtaagatcgt    120
gatgtgaaag taggtattaa atataggtgg attatctatc ttttttgctt attccggagg    180 tttttttga atttcaatgg ttggaattgg agtgtttcac atagaaattc ctttgttgca    240
atgaaaatgt atctcattga attcatatat ttttaatgcc caggctgact aagctagcag    300
catagcaaga aaaggtaaca gtactaatta ggagaaactt taccactctt aaagagatac    360 aaaattttc taatgtaaaa ttgggtaaag gtgccaattt ttactataca agatgtactt    420
ctaatacata ggtcaaatta ctaactagtt aaactatgtt tgaaacaccg gaaaaattac    480
tacttccctc cattttatat tataagttgt tttaactttt tttaagttga atttcttta    540 atttgatcaa gttataaaa aaacatatta gccaaaatat atttaatgtt agatttaagg    600
aaactaattt gatgtttgag atgttactaa attttaaac tttgataaat caaaacactt    660

```
ataatatgaa acggagaacc cggagagata gttcctacga attttgattt tttttttgac      720
aattccaaga aaaccccctat gaaattcatg ggttccaaaa tctcttgaac caattgtgaa     780
```

```
ataatatgaa acggagaacc cggagagata gttcctacga attttgattt tttttttgac      720
aattccaaga aaaccccctat gaaattcatg ggttccaaaa tctcttgaac caattgtgaa     780
tagagctttt ttttttagaa ctgtcaatta acagagttaa tggcattatc agatcacaga      840
gtaatatcat agtctgtgta aattcaagat cttaatccat attgatttga agtagcaaat      900
gcaaggaaca aagaggagaa gaagaaaaaa aatggttggc tgctgcaata gtgggatcac      960
cacccaaaac catctctttc caaagcgaag ccgaccaccg ccatcatggc cacctccacc     1020
tccacccatg gccatggcca tctcctccct tcgactcctc ctcctccccc ctccgacctc     1080
ctcatcatga                                                            1090

<210> SEQ ID NO 4
<211> LENGTH: 26
<212> TYPE: DNA
<213> ORGANISM: Oryza sp.

<400> SEQUENCE: 4
ggaggagtcg aagggaggag atggcc                                            26

<210> SEQ ID NO 5
<211> LENGTH: 12
<212> TYPE: DNA
<213> ORGANISM: Oryza sp.

<400> SEQUENCE: 5
atggccatgg  cc                                                          12

<210> SEQ ID NO 6
<211> LENGTH: 505
<212> TYPE: PRT
<213> ORGANISM: Arabidopsis sp.

<400> SEQUENCE: 6
```

```
Pro Ser Ile Leu Cys His Leu Pro Ser Leu His Ser Leu Ser Leu Tyr
  1               5                  10                  15

Asn Asn Ser Ile Asn Gly Ser Leu Ser Ala Asp Asp Phe Asp Thr Cys
             20                  25                  30

His Asn Leu Ile Ser Leu Asp Leu Ser Glu Asn Leu Leu Val Gly Ser
         35                  40                  45

Ile Pro Lys Ser Leu Pro Phe Asn Leu Pro Asn Leu Lys Phe Leu Glu
     50                  55                  60

Ile Ser Gly Asn Asn Leu Ser Asp Thr Ile Pro Ser Ser Phe Gly Glu
 65                  70                  75                  80

Phe Arg Lys Leu Glu Ser Leu Asn Leu Ala Gly Asn Phe Leu Ser Gly
                 85                  90                  95

Thr Ile Pro Ala Ser Leu Gly Asn Val Thr Thr Leu Lys Glu Leu Lys
            100                 105                 110

Leu Ala Tyr Asn Leu Phe Ser Pro Ser Gln Ile Pro Ser Gln Leu Gly
        115                 120                 125

Asn Leu Thr Glu Leu Gln Val Leu Trp Leu Ala Gly Cys Asn Leu Val
    130                 135                 140

Gly Pro Ile Pro Pro Ser Leu Ser Arg Leu Thr Ser Leu Val Asn Leu
145                 150                 155                 160

Asp Leu Thr Phe Asn Gln Leu Thr Gly Ser Ile Pro Ser Trp Ile Thr
                165                 170                 175

Gln Leu Lys Thr Val Glu Gln Ile Glu Leu Phe Asn Asn Ser Phe Ser
            180                 185                 190
```

```
Gly Glu Leu Pro Glu Ser Met Gly Asn Met Thr Thr Leu Lys Arg Phe
            195                 200                 205

Asp Ala Ser Met Asn Lys Leu Thr Gly Lys Ile Pro Asp Asn Leu Asn
210                 215                 220

Leu Leu Asn Leu Glu Ser Leu Asn Leu Phe Glu Asn Met Leu Glu Gly
225                 230                 235                 240

Pro Leu Pro Glu Ser Ile Thr Arg Ser Lys Thr Leu Ser Glu Leu Lys
                245                 250                 255

Leu Phe Asn Asn Arg Leu Thr Gly Val Leu Pro Ser Gln Leu Gly Ala
            260                 265                 270

Asn Ser Pro Leu Gln Tyr Val Asp Leu Ser Tyr Asn Arg Phe Ser Gly
            275                 280                 285

Glu Ile Pro Ala Asn Val Cys Gly Glu Gly Lys Leu Glu Tyr Leu Ile
            290                 295                 300

Leu Ile Asp Asn Ser Phe Ser Gly Glu Ile Ser Asn Asn Leu Gly Lys
305                 310                 315                 320

Cys Lys Ser Leu Thr Arg Val Arg Leu Ser Asn Asn Lys Leu Ser Gly
                325                 330                 335

Gln Ile Pro His Gly Phe Trp Gly Leu Pro Arg Leu Ser Leu Leu Glu
            340                 345                 350

Leu Ser Asp Asn Ser Phe Thr Gly Ser Ile Pro Lys Thr Ile Ile Gly
            355                 360                 365

Ala Lys Asn Leu Ser Asn Leu Arg Ile Ser Lys Asn Arg Phe Ser Gly
            370                 375                 380

Ser Ile Pro Asn Glu Ile Gly Ser Leu Asn Gly Ile Ile Glu Ile Ser
385                 390                 395                 400

Gly Ala Glu Asn Asp Phe Ser Gly Glu Ile Pro Glu Ser Leu Val Lys
                405                 410                 415

Leu Lys Gln Leu Ser Arg Leu Asp Leu Ser Lys Asn Gln Leu Ser Gly
            420                 425                 430

Glu Ile Pro Arg Glu Leu Arg Gly Trp Lys Asn Leu Asn Glu Leu Asn
            435                 440                 445

Leu Ala Asn Asn His Leu Ser Gly Ile Pro Lys Glu Val Gly Ile
450                 455                 460

Leu Pro Val Leu Asn Tyr Leu Asp Leu Ser Ser Asn Gln Phe Ser Gly
465                 470                 475                 480

Glu Ile Pro Leu Glu Leu Gln Asn Leu Lys Leu Asn Val Leu Asn Leu
            485                 490                 495

Ser Tyr Asn His Leu Ser Gly Lys Ile
            500                 505

<210> SEQ ID NO 7
<211> LENGTH: 466
<212> TYPE: PRT
<213> ORGANISM: Arabidopsis sp.

<400> SEQUENCE: 7

Leu Asn Leu Ser Asp Leu Asn Leu Asp Gly Glu Ile Ser Pro Ala Ile
 1               5                  10                  15

Gly Asp Leu Lys Ser Leu Leu Ser Ile Asp Leu Arg Gly Asn Arg Leu
                20                  25                  30

Ser Gly Gln Ile Pro Asp Glu Ile Gly Asp Cys Ser Ser Leu Gln Asn
            35                  40                  45

Leu Asp Leu Ser Phe Asn Glu Leu Ser Gly Asp Ile Pro Phe Ser Ile
```

-continued

```
            50                  55                  60
Ser Lys Leu Lys Gln Leu Glu Gln Leu Ile Leu Lys Asn Asn Gln Leu
65                      70                  75                  80
Ile Gly Pro Ile Pro Ser Thr Leu Ser Gln Ile Pro Asn Leu Lys Ile
                    85                  90                  95
Leu Asp Leu Ala Gln Asn Lys Leu Ser Gly Glu Ile Pro Arg Leu Ile
                100                 105                 110
Tyr Trp Asn Glu Val Leu Gln Tyr Leu Gly Leu Arg Gly Asn Asn Leu
            115                 120                 125
Val Gly Asn Ile Ser Pro Asp Leu Cys Gln Leu Thr Gly Leu Trp Tyr
130                 135                 140
Phe Asp Val Arg Asn Asn Ser Leu Thr Gly Ser Ile Pro Glu Thr Ile
145                 150                 155                 160
Gly Asn Cys Thr Ala Phe Gln Val Leu Asp Leu Ser Tyr Asn Gln Leu
                165                 170                 175
Thr Gly Glu Ile Pro Phe Asp Ile Gly Phe Leu Gln Val Ala Thr Leu
                180                 185                 190
Ser Leu Gln Gly Asn Gln Leu Ser Gly Lys Ile Pro Ser Val Ile Gly
            195                 200                 205
Leu Met Gln Ala Leu Ala Val Leu Asp Leu Ser Gly Asn Leu Leu Ser
    210                 215                 220
Gly Ser Ile Pro Pro Ile Leu Gly Asn Leu Thr Phe Thr Glu Lys Leu
225                 230                 235                 240
Tyr Leu His Ser Asn Lys Leu Thr Gly Ser Ile Pro Pro Glu Leu Gly
                245                 250                 255
Asn Met Ser Lys Leu His Tyr Leu Glu Leu Asn Asp Asn His Leu Thr
            260                 265                 270
Gly His Ile Pro Pro Glu Leu Gly Lys Leu Thr Asp Leu Phe Asp Leu
        275                 280                 285
Asn Val Ala Asn Asn Asp Leu Glu Gly Pro Ile Pro Asp His Leu Ser
    290                 295                 300
Ser Cys Thr Asn Leu Asn Ser Leu Asn Val His Gly Asn Lys Phe Ser
305                 310                 315                 320
Gly Thr Ile Pro Arg Ala Phe Gln Lys Leu Glu Ser Met Thr Tyr Leu
                325                 330                 335
Asn Leu Ser Ser Asn Asn Ile Lys Gly Pro Ile Pro Val Glu Leu Ser
            340                 345                 350
Arg Ile Gly Asn Leu Asp Thr Leu Asp Leu Ser Asn Asn Lys Ile Asn
        355                 360                 365
Gly Ile Ile Pro Ser Ser Leu Gly Asp Leu Glu His Leu Leu Lys Met
    370                 375                 380
Asn Leu Ser Arg Asn His Ile Thr Gly Val Val Pro Gly Asp Phe Gly
385                 390                 395                 400
Asn Leu Arg Ser Ile Met Glu Ile Asp Leu Ser Asn Asn Asp Ile Ser
                405                 410                 415
Gly Pro Ile Pro Glu Glu Leu Asn Gln Leu Gln Asn Ile Ile Leu Leu
            420                 425                 430
Arg Leu Glu Asn Asn Asn Leu Thr Gly Asn Val Gly Ser Leu Ala Asn
        435                 440                 445
Cys Leu Ser Leu Thr Val Leu Asn Val Ser His Asn Asn Leu Val Gly
    450                 455                 460
Asp Ile
465
```

<210> SEQ ID NO 8
<211> LENGTH: 554
<212> TYPE: PRT
<213> ORGANISM: Oryza sp.

<400> SEQUENCE: 8

```
Val Val Lys Leu Leu Arg Ser Ser Asn Leu Ser Gly Ile Ile Ser
 1               5                  10                  15

Pro Ser Leu Gly Asn Leu Ser Phe Leu Arg Glu Leu Asp Leu Gly Asp
                20                  25                  30

Asn Tyr Leu Ser Gly Glu Ile Pro Pro Glu Leu Ser Arg Leu Ser Arg
            35                  40                  45

Leu Gln Leu Leu Glu Leu Ser Asp Asn Ser Ile Gln Gly Ser Ile Pro
 50                  55                  60

Ala Ala Ile Gly Ala Cys Thr Lys Leu Thr Ser Leu Asp Leu Ser His
 65                  70                  75                  80

Asn Gln Leu Arg Gly Met Ile Pro Arg Glu Ile Gly Ala Ser Leu Lys
                85                  90                  95

His Leu Ser Asn Leu Tyr Leu Tyr Lys Asn Gly Leu Ser Gly Glu Ile
            100                 105                 110

Pro Ser Ala Leu Gly Asn Leu Thr Ser Leu Gln Glu Phe Asp Leu Ser
            115                 120                 125

Phe Asn Arg Leu Ser Gly Ala Ile Pro Ser Ser Leu Gly Gln Leu Ser
130                 135                 140

Ser Leu Leu Thr Met Asn Leu Gly Gln Asn Asn Leu Ser Gly Met Ile
145                 150                 155                 160

Pro Asn Ser Ile Trp Asn Leu Ser Ser Leu Arg Ala Phe Ser Val Arg
                165                 170                 175

Glu Asn Lys Leu Gly Gly Met Ile Pro Thr Asn Ala Phe Lys Thr Leu
            180                 185                 190

His Leu Leu Glu Val Ile Asp Met Gly Thr Asn Arg Phe His Gly Lys
            195                 200                 205

Ile Pro Ala Ser Val Ala Asn Ala Ser His Leu Thr Val Ile Gln Ile
210                 215                 220

Tyr Gly Asn Leu Phe Ser Gly Ile Ile Thr Ser Gly Phe Gly Arg Leu
225                 230                 235                 240

Arg Asn Leu Thr Glu Leu Tyr Leu Trp Arg Asn Leu Phe Gln Thr Arg
                245                 250                 255

Glu Gln Asp Asp Trp Gly Phe Ile Ser Asp Leu Thr Asn Cys Ser Lys
            260                 265                 270

Leu Gln Thr Leu Asn Leu Gly Glu Asn Asn Leu Gly Gly Val Leu Pro
            275                 280                 285

Asn Ser Phe Ser Asn Leu Ser Thr Ser Leu Ser Phe Leu Ala Leu Glu
290                 295                 300

Leu Asn Lys Ile Thr Gly Ser Ile Pro Lys Asp Ile Gly Asn Leu Ile
305                 310                 315                 320

Gly Leu Gln His Leu Tyr Leu Cys Asn Asn Phe Arg Gly Ser Leu
                325                 330                 335

Pro Ser Ser Leu Gly Arg Leu Lys Asn Leu Gly Ile Leu Leu Ala Tyr
            340                 345                 350

Glu Asn Asn Leu Ser Gly Ser Ile Pro Leu Ala Ile Gly Asn Leu Thr
            355                 360                 365

Glu Leu Asn Ile Leu Leu Leu Gly Thr Asn Lys Phe Ser Gly Trp Ile
```

```
                        370                 375                 380
Pro Tyr Thr Leu Ser Asn Leu Thr Asn Leu Leu Ser Leu Gly Leu Ser
385                 390                 395                 400

Thr Asn Asn Leu Ser Gly Pro Ile Pro Ser Glu Leu Phe Asn Ile Gln
                405                 410                 415

Thr Leu Ser Ile Met Ile Asn Val Ser Lys Asn Asn Leu Glu Gly Ser
                420                 425                 430

Ile Pro Gln Glu Ile Gly His Leu Lys Asn Leu Val Glu Phe His Ala
            435                 440                 445

Glu Ser Asn Arg Leu Ser Gly Lys Ile Pro Asn Thr Leu Gly Asp Cys
        450                 455                 460

Gln Leu Leu Arg Tyr Leu Tyr Leu Gln Asn Asn Leu Leu Ser Gly Ser
465                 470                 475                 480

Ile Pro Ser Ala Leu Gly Gln Leu Lys Gly Leu Glu Thr Leu Asp Leu
                485                 490                 495

Ser Ser Asn Asn Leu Ser Gly Gln Ile Pro Thr Ser Leu Ala Asp Ile
                500                 505                 510

Thr Met Leu His Ser Leu Asn Leu Ser Phe Asn Ser Phe Val Gly Glu
            515                 520                 525

Val Pro Thr Ile Gly Ala Phe Ala Ala Ala Ser Gly Ile Ser Ile Gln
        530                 535                 540

Gly Asn Ala Lys Leu Cys Gly Gly Ile Pro
545                 550
```